(12) United States Patent  (10) Patent No.: US 11,464,413 B2
Abd-Elmoniem et al.  (45) Date of Patent: Oct. 11, 2022

(54) IMAGING AND DIAGNOSTIC METHODS, SYSTEMS, AND COMPUTER-READABLE MEDIA

(71) Applicant: The United States of America, as represented by the Secretary, Department of Health & Human Services, Rockville, MD (US)

(72) Inventors: Khaled Z. Abd-Elmoniem, Silver Spring, MD (US); Ahmed M. Gharib, Bethesda, MD (US); Roderic I. Pettigrew, Bethesda, MD (US)

(73) Assignee: The United States of America as represented by Secretary, Department of Health and Human Services, Bethesda, MD (US)

( * ) Notice: Subject to any disclaimer, the term of this patent is extended or adjusted under 35 U.S.C. 154(b) by 1390 days.

(21) Appl. No.: 14/423,037

(22) PCT Filed: Aug. 21, 2013

(86) PCT No.: PCT/US2013/055997
§ 371 (c)(1),
(2) Date: Feb. 20, 2015

(87) PCT Pub. No.: WO2014/031754
PCT Pub. Date: Feb. 27, 2014

(65) Prior Publication Data
US 2015/0223703 A1   Aug. 13, 2015

Related U.S. Application Data

(60) Provisional application No. 61/692,191, filed on Aug. 22, 2012.

(51) Int. Cl.
*G01R 33/563*  (2006.01)
*G01R 33/56*  (2006.01)
(Continued)

(52) U.S. Cl.
CPC .......... *A61B 5/02007* (2013.01); *A61B 5/004* (2013.01); *A61B 5/055* (2013.01);
(Continued)

(58) Field of Classification Search
None
See application file for complete search history.

(56) References Cited

U.S. PATENT DOCUMENTS 6,700,374 B1 * 3/2004 Wu .................. G01R 33/56554
324/306
7,412,277 B1    8/2008 Saranathan et al.
(Continued)

FOREIGN PATENT DOCUMENTS

JP    2012-105982    6/2012

OTHER PUBLICATIONS

Priest et al., "Coronary Vessel-Wall and Lumen Imaging Using Radial k-Space Acquisition with MRI at 3 Tesla", Eur. Radiol. (2007) 17: pp. 339-346.*

(Continued)

*Primary Examiner* — Katherine L Fernandez
*Assistant Examiner* — Farouk A Bruce
(74) *Attorney, Agent, or Firm* — Leydig, Voit & Mayer, Ltd

(57) ABSTRACT

One aspect of the present subject matter provides an imaging method including: receiving a trigger signal; after a period substantially equal to a trigger delay minus an inversion delay, applying a non-selective inversion radiofrequency pulse to a region of interest followed by a slice-selective reinversion radiofrequency pulse to a slice of the region of interest of a subject; and after lapse of the trigger delay commenced at the cardiac cycle signal, acquiring a plurality of time-resolved images of the slice of the region of interest from an imaging device.

24 Claims, 10 Drawing Sheets

(51) Int. Cl.
*A61B 5/352* (2021.01)
*G01R 33/567* (2006.01)
*A61B 5/02* (2006.01)
*A61B 5/00* (2006.01)
*A61B 5/055* (2006.01)

(52) U.S. Cl.
CPC ............ *A61B 5/352* (2021.01); *A61B 5/7207* (2013.01); *A61B 5/7221* (2013.01); *A61B 5/7278* (2013.01); *A61B 5/7285* (2013.01); *A61B 5/7425* (2013.01); *G01R 33/5602* (2013.01); *G01R 33/56325* (2013.01); *A61B 2576/02* (2013.01); *G01R 33/5635* (2013.01); *G01R 33/5673* (2013.01); *G01R 33/5676* (2013.01)

(56) References Cited

U.S. PATENT DOCUMENTS

| | | | | |
|---|---|---|---|---|
| 7,941,204 | B1* | 5/2011 | Wang | G01R 33/4824 600/420 |
| 2004/0133098 | A1* | 7/2004 | Yarnykh | G01R 33/5607 324/306 |
| 2005/0010104 | A1 | 1/2005 | Fayad et al. | |
| 2006/0253015 | A1 | 11/2006 | Nezafat et al. | |
| 2007/0255129 | A1* | 11/2007 | Du | G01R 33/4824 600/410 |
| 2008/0012564 | A1* | 1/2008 | Lin | G01R 33/4824 324/309 |
| 2012/0083687 | A1* | 4/2012 | Parker | A61B 5/024 600/419 |
| 2012/0123240 | A1* | 5/2012 | Silber | A61B 5/02007 600/410 |

OTHER PUBLICATIONS

Abd-Elmoniem et al., "Phase-Sensitive Black-Blood Coronary Vessel Wall Imaging", Magnetic Resonance in Medicine 63:1021-1030 (2010) (Year: 2010).*

Stehning, et al. "Advances in Coronary MRA from Vessel Wall to Whole Heart Imaging", Magn. Reson. Med. Scil, vol. 6, No. 3, pp. 157-170, 2007 (Year: 2007).*

Andrew N Priest et al.: "Coronary vessel-wall and lumen imaging using radial k-space acquisition with MRI at 3 Tesla", European Radiology, Springer, Berlin, DE, vol. 17, No. 2, Oct. 5, 2006 (Oct. 5, 2006), pp. 339-346, XP019473259, ISSN: 1432-1084 abstract p. 339, col. 1 p. 340, col. 2, paragraphs 2, 3 p. 341; figure 1.

International Search Report from PCT/2013/055997 dated Feb. 14, 2014.

Communication pursuant to Article 94(3) EPC from European Application No. 13759362.0, dated Dec. 10, 2019, 5 pages.

* cited by examiner (SEE FLOWCHART IN FIG. 4)

(a)

(b)

IMAGING AND DIAGNOSTIC METHODS, SYSTEMS, AND COMPUTER-READABLE MEDIA

CROSS-REFERENCE TO RELATED APPLICATIONS

This application claims priority to U.S. Provisional Patent Application Ser. No. 61/692,191, filed Aug. 22, 2012. The entire content of this application is hereby incorporated by reference herein.

GOVERNMENT INTEREST STATEMENT

The present subject matter was made with U.S. government support. The U.S. government has certain rights in this subject matter.

FIELD

The present subject matter relates generally to magnetic resonance imaging (MRI) systems, algorithms, and methods for imaging of vessel walls and measuring vessel wall thickness (including, for example, a coronary arterial wall).

BACKGROUND

Atherosclerosis is an underlying mechanism of ischemic heart disease and stroke, which represent the most common cause of death in the United States. Atherogenesis starts from the deposition of ApoB-containing lipoproteins, such as low-density lipoproteins and chylomicron remnants, in the intima of the arterial wall. Macrophages then take up the deposited lipoproteins and transform into foam cells. The presence of foam cells in the arterial intima contributes to thickening of the vessel wall and is a hallmark feature of atherosclerosis. Continued accumulation of lipid and lipid-laden foam cells, and the succeeded proliferation of smooth muscle and connective tissue give rise to atherosclerotic plaques and further thickening of vessel walls. Rupture of a plaque triggers thrombosis and/or embolism that can cause luminal occlusion in coronary or cerebral arteries, resulting in heart attack and stroke.

MRI methods for assessing vascular health can provide further insight in the understanding of atherosclerosis and its response to various therapies (1, 2, 4-7). However, technical challenges still hinder vessel wall imaging for routine clinical utilization, including, for example aperiodic intrinsic cardiac and chest wall motions and blood flow-induced motion. Thus, there remains a need for an MRI imaging method that can reliably image vessels and vessel wall thickness, particularly in the presence of aperiodic intrinsic motion.

SUMMARY OF THE PRESENT SUBJECT MATTER

One aspect of the present subject matter provides an imaging method including: receiving a trigger signal; after a period substantially equal to a trigger delay minus an inversion delay, applying a non-selective inversion radiofrequency pulse to a region of interest followed by a slice-selective reinversion radiofrequency pulse to a slice of the region of interest of a subject; and after lapse of the trigger delay commenced at the cardiac cycle signal, acquiring a plurality of time-resolved images of the slice of the region of interest from an imaging device.

This aspect of the present subject matter can have a variety of embodiments. The trigger signal can be a cardiac cycle signal. The cardiac cycle signal can be an R-wave. The trigger delay can correspond to the time period between the cardiac cycle signal and a period of minimal myocardial motion.

The region of interest can be a blood vessel. The region of interest can be a coronary artery. The region of interest can be a peripheral vessel. The region of interest can be selected from the group consisting of: a carotid artery and a femoral artery.

The trigger delay and the inversion delay can be specified by a human. The trigger delay and the inversion delay can be calculated by a computer.

The plurality of images can be consecutive.

A temporal offset between the plurality of images can be substantially uniform. The temporal offset can be between about 5 ms and about 50 ms. The temporal offset can be about 25 ms.

The inversion delay can be about 150 ms.

The plurality of images can be captured between about 150 ms and about 225 ms after application of the non-selective inversion radiofrequency pulse.

The method can further comprise storing the plurality of time-resolved images in a computer-readable medium.

The method can further include: presenting the plurality of time-resolved images to a user; receiving a selection of one or more high quality images from the plurality of time-resolved images; and calculating vessel thickness based on the one or more high quality images.

In another embodiment, at least 75% of a vessel of interest is visible in the one or more high quality images.

The method can further include: applying a navigator pulse directly before acquiring the plurality of time-resolved images; tracking lung motion; and compensating for lung-motion-induced changes in an anatomical location of the region of interest.

The method can further include instructing the subject to hold their breath during acquisition of the plurality of time-resolved images.

The method can further include instructing the subject to breath normally during acquisition of the plurality of time-resolved images.

The method can include repeating the obtaining, applying, and acquiring steps at an interval selected from the group consisting of: every cardiac cycle, every other cardiac cycle, and every nth cardiac cycle, wherein n is a positive integer.

In one embodiment, at least 75% of a vessel of interest is visible in at least one of the plurality of time-resolved images in at least 90% of instances of the method.

The slice of the region of interest can contain a cross-section of a vessel and the method can further include calculating a thickness of the vessel.

The slice can be a two-dimensional slice. The slice can be a three-dimensional slice.

Another aspect of the present subject matter provides a non-transitory computer readable medium containing program instructions executable by a processor. The computer readable medium includes: program instructions that receive a trigger signal; program instructions that, after a period substantially equal to a trigger delay minus an inversion delay, apply a non-selective inversion radiofrequency pulse to a region of interest followed by a slice-selective reinversion radiofrequency pulse to a slice of the region of interest of a subject; and after lapse of the trigger delay commenced at the cardiac cycle signal, acquire a plurality of time-resolved images of the slice of the region of interest from an imaging device.

Another aspect of the present subject matter provides a magnetic resonance imaging device including: a magnetic field gradient controller programmed to control operation of a magnetic field gradient amplifier to alter a spinning frequency of atomic nuclei within a subject; a radio frequency pulse controller programmed to control operation of a radiofrequency transmitter to apply radiofrequency pulses to a region of interest within the subject; an analog/digital signal converter programmed to convert analog signals received by a radiofrequency receiver coil; and an imaging sequence controller programmed to: receive a trigger signal; instruct the radiofrequency pulse controller to, after a period substantially equal to a trigger delay minus an inversion delay, apply a non-selective inversion radiofrequency pulse to a region of interest followed by a slice-selective reinversion radiofrequency pulse to a slice of the region of interest; and instruct the analog/digital signal converter to, after lapse of the trigger delay commenced at the trigger signal, acquire a plurality of time-resolved images of the slice of the region of interest from an imaging device.

This aspect of the present subject matter can have a variety of embodiments. In one embodiment, at least 75% of a vessel of interest is visible in at least one of the plurality of time-resolved images in at least 90% of uses of the device.

Another aspect of the present subject matter provides an imaging method including: receiving a magnetic resonance phase map image of a vessel of interest; receiving a plurality of traced pixels substantially corresponding to a centerline of the vessel of interest; and identifying inner and outer boundaries of the vessel of interest.

This aspect of the present subject matter can have a variety of embodiments. The identifying step further include: identifying a peak intensity value in a local pixel region surrounding each traced pixel; calculating a direction of maximum intensity variation for each point along the centerline of the vessel of interest; fitting a one-dimensional distribution-shape model across the vessel wall along the direction of maximum intensity variation; and identifying the inner and outer boundaries as points having a steepest pixel intensity gradient within the one-dimensional distribution-shape model on each side of centerline.

The method can further include calculating vessel wall thickness as an average distance between the inner and outer boundaries of the vessel of interest along a circumference of the vessel wall. The one-dimensional distribution-shape model can be a Gaussian model. The local pixel region can be a 3×3 pixel region surrounding each traced pixel. The vessel of interest can be a blood vessel.

The method can further include repeating the method for one or more time-lapsed images. The method can further include selecting a lowest vessel wall thickness from among the time-lapsed images as a representative thickness of the vessel of interest.

Another aspect of the present subject matter includes a non-transitory computer readable medium containing program instructions executable by a processor. The computer readable medium includes: program instructions that receive a magnetic resonance phase map image of a vessel of interest; program instructions that receive a plurality of traced pixels substantially corresponding to a centerline of the vessel of interest; and program instructions that identify inner and outer boundaries of the vessel of interest.

Another aspect of the present subject matter includes a method of diagnosing vascular disease. The method includes: receiving a plurality of time-resolved images of a slice of a blood vessel of interest; calculating a vessel wall thickness for at least a subset of the plurality of time-resolved images; determining a minimum vessel wall thickness among the vessel wall thickness calculated for subset; and rendering a diagnosis of vascular disease if the minimum vessel wall thickness is above a threshold value.

This aspect of the present subject matter can have a variety of embodiments. The plurality of time-resolved images can include greater than three images. The plurality of time-resolved images can include between three images and five images.

The subset of the plurality of time-resolved images can include greater than three images. The subset of the plurality of time-resolved images can include between three and five images.

The threshold value can be about 1.24 mm. The threshold value can be selected from the group consisting of: about 1.30 mm, about 1.35 mm, about 1.40 mm, and about 1.45 mm.

The vascular disease can be atherosclerosis. The blood vessel can be a coronary artery.

Another aspect of the present subject matter provides a non-transitory computer readable medium containing program instructions executable by a processor. The computer readable medium includes: program instructions that receive a plurality of time-resolved images of a slice of a blood vessel of interest; program instructions that calculate a vessel wall thickness for at least a subset of the plurality of time-resolved images; program instructions that determine a minimum vessel wall thickness among the vessel wall thickness calculated for subset; and program instructions that render a diagnosis of vascular disease if the minimum vessel wall thickness is above a threshold value.

BRIEF DESCRIPTION OF THE DRAWINGS

For a fuller understanding of the nature and desired objects of the present subject matter, reference is made to the following detailed description taken in conjunction with the accompanying drawing figures. Reference numerals herein are presented in brackets and should be distinguished from citations, which are presented in parentheses. Like reference numerals denote corresponding parts throughout the several views. Reference numerals are denoted in two-digit format in the figures, with the FIG. number prepended when used in the specification. For example, reference numeral 8 in FIG. 1 appears in the specification as reference numeral [108] and reference number 18 in FIG. 2 appears in the specification as reference numeral [218].

FIG. 6(a) depicts modulus (DIR), phase, and TRAPD signed-magnitude images. FIG. 6(b) depicts signal intensity inside and outside the lumen. FIG. 6(c) depicts DIR and TRAPD tissue-lumen contrasts. FIG. 6(d) TRAPD and modulus-only cross-sectional signal intensity profile through the center of the phantom tube at three different values of TI. Broken and continuous curves correspond to modulus and TRAPD signed reconstruction, respectively.

DEFINITIONS

Figure 1:
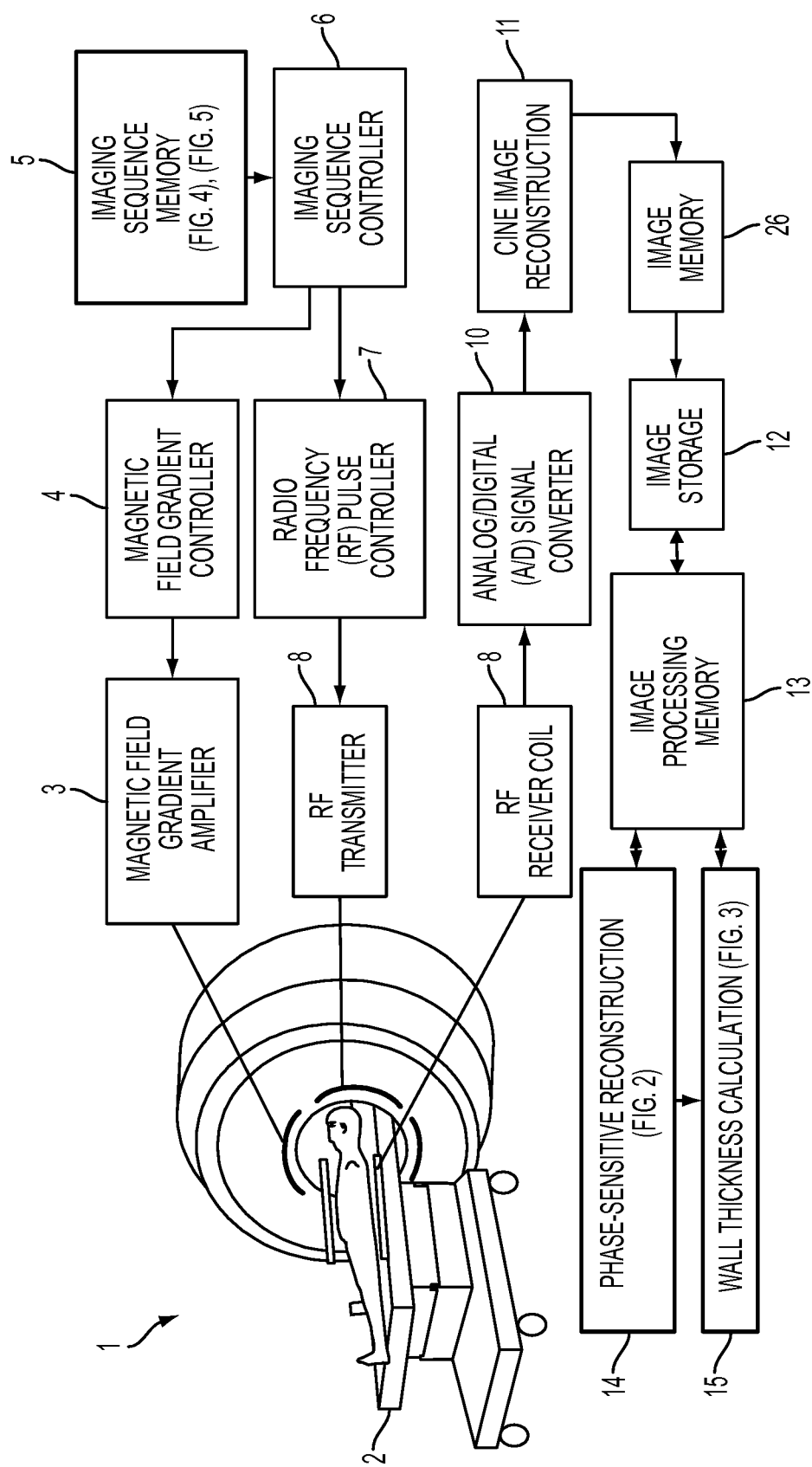
FIG. 1 depicts a schematic diagram of one example of an MRI system for time-resolved acquisitions of phase-sensitive dual-inversion recovery (TRAPD) according to the present subject matter.

For the purposes of this application, the following terms will have the following meanings unless specifically stated otherwise:

The phrase "Magnetic Resonance Imaging" or "MRI" as used herein means the process by which certain nuclei, when placed in a magnetic field, absorb and release energy in the form of radio waves that are analyzed by a computer, thereby producing an image (e.g., of structures, human anatomy, and physiological information). The present subject matter and methods can be employed with MRI generated with MRI equipment from any manufacturer. In some embodiments, the MRI equipment or scanner [101] shall have a scanner housing with a magnet with a typical magnetic field ($B_0$), ranging from about 0.5 to about 7 Tesla or higher, positioned inside the housing. In biomedical applications, the subject to be imaged (e.g., a human body) lies on the scanner table [102] or is disposed within the bore of the MRI equipment and the hydrogen and other nuclei in the subject are realigned in certain directions. Magnetic field gradient coils [103] are arranged near the imaged subject to superimpose on $B_0$ an additional selected spatially-varying magnetic field. One or more radiofrequency (RF) coils [108] are arranged inside the bore of the magnet to transmit RF excitation and inversion pulses ($B_1$). The RF coils also measure the RF magnetic resonance signal emitted from the imaged subject. The gradient coils [103] and the RF transmitter coils [108] are turned on and off at specific strengths and for specific duration according in a predetermined sequence of actions collectively called an imaging sequence [106]. At specific time points during the execution of the imaging sequence, the RF receiver coils [108] measure the RF signals emitted from the body [102]. Images of structures such as body parts or organs are created from the measured RF signals during or after the completion of the imaging sequence [111].

The term "vessel" as used herein refers to any structure capable of receiving a fluid. In biomedical applications of the present subject matter, exemplary vessels can include a tubular tissue within the cardiac, coronary, renal, peripheral vascular, gastrointestinal, pulmonary, lymphatic, urinary and neurovascular systems and the brain. In certain embodiments, the vessels are vascular blood vessels. In one embodiment, the vessels are coronary blood vessels, including the coronary artery. In another embodiment, the vessels are peripheral vessels such as the carotid or femoral arteries. In some embodiments, the methods of the present subject matter can image vessel wall thickness in vessels ranging in size down to sub-millimeter in diameter. As discussed throughout, the invention can be applied to image other vessels such as tubing used in commercial or industrial equipment and drill strings used in petroleum drilling operations.

The phrase "vessel wall thickness" as used herein means the distance measured across a vessel wall from the inside luminal surface to the exterior surface. Generally, vessel wall thickness is viewed from an approximate cross-sectional view or a longitudinal view of the vessel being imaged.

The phrase "cinematic imaging" or "cine" as used herein means an acquisition of multiple consecutive images of a vessel in a regular or periodic time frame.

The phrase "dual-inversion recovery" as used herein means the magnetic resonance imaging sequences in which the acquisition of data is preceded by two or more magnetization inversion RF pulses.

The phrase "phase-sensitive dual-inversion recovery" as used herein means a dual-inversion recovery imaging sequence in which the signal intensity of any pixel in the acquired images will be assigned either negative or positive sign or label.

The phrase "phase-sensitive reconstruction" as used herein means the creation of an image in which the pixels are assigned both a signal intensity value and a positive or negative label.

The phrase "inhomogeneity-free phase image" as used herein means a phase image in which the phase component related to magnetic field inhomogeneity has been suppressed.

The phrase "modulus magnitude image" as used herein means an image showing the absolute or the modulus magnitude value of the complex-value data.

The phrase "signed-magnitude image" as used herein means an image in which the signal intensity of a pixel can be positive or negative or has a positive modulus magnitude and a positive or a negative label.

The phrase "local region-growing algorithm" as used herein means an algorithm that takes as an input an initial region of one or more points and the algorithm iteratively searches around and near that region for points that share certain features with the points included in the region. The region gradually increases its size until a certain stopping criteria is reached.

The phrase "navigator-guided mode" as used herein refers to a technique that utilizes an additional quick MR prepulse to measure the position of, for example, the diaphragm before data collection. The prepulse sequence images a small area perpendicular to the structure that is moving (e.g., due to the subject's breathing). After data acquisition, the position of the interface is automatically recorded and imaging data are only accepted when the position of the interface falls within a range of prespecified values.

The phrase "cardiac cycle" as used herein means the predictable or periodic events related to cardiac motion or cardiac electrophysiology.

The phrase "cardiac cycle signal" as used herein means a portion of the cardiac cycle that can be detected, and which is a predictable or periodic event related to cardiac motion or cardiac electrophysiology that can be detected. Non-limiting examples of a cardiac cycle signal can be selected from the cardiac RR interval, P wave, PR interval, PR segment, QRS complex, R wave, J point, ST segment, T wave, ST interval, QT interval, U wave, J wave, portions of the same, and combinations of the same. In one embodiment, the cardiac cycle signal is the R-wave. The cardiac cycle signal can be generated based on any periodic event including, but not limited to, the subject's heart motion, an electrocardiogram of the subject, or from a synthetic source such as a software algorithm or a hardware circuit.

The term "periodic" as used herein means at regular or predictable intervals. Non-limiting examples of detecting periodic cardiac cycles include detecting each cardiac cycle, every other cardiac cycle, every third cardiac cycle, or every n-th cardiac cycle (wherein n is a positive integer). The regular period of a cardiac cycle can be detected by using one or more of the cardiac cycle signals as time markers of the predefined periodicity sought. As discussed above in the context of a "cardiac cycle signal," period signals (e.g., corresponding to the cardiac cycle) can be generated by internal or external sources.

The phrase "trigger signal" as used herein means a signal generated in response to an event affecting the shape or position of a vessel. For example, a trigger signal can be a cardiac cycle signal, from which the position of a cardiac vessel at a later time can be inferred. In another example, the trigger signal can be a blood pressure pulse, from which the position and/or shape of a peripheral vessel such as a carotid artery can be inferred. In experimental, robotic, or industrial applications, the trigger signal can be a pressure pulse reflecting operation of a fluid pump. As discussed above in the context of "cardiac cycle signal" and "periodic," the trigger signal can be measured directly (i.e., the shape and/or position of the vessel can be inferred based on direct measurement of a pressure pulse) or indirectly (i.e., an electronic trigger signal can be generated by a device that measures the pressure pulse).

The phrase "one-dimensional distribution-shape model" as used herein means a mathematical model capable of providing a predictive distribution for a set of data points along a predefined line. Non-limiting examples of one-dimensional distribution-shape model can include the Gaussian model and the Lorentzian model.

The term "memory" as used herein encompasses both volatile memory (e.g., random access memory and the like) and non-volatile memory (e.g., read-only memory, hard disks, floppy discs, magnetic tape, optical discs, paper table, punch cards, and the like).

The term "subject" as used herein shall be understood to include any animal including mammals including, but not limited to, humans and primates.

The term "slice" as used herein shall be understood to include both two-dimensional and three-dimensional images of a vessel. Preferably, a slice is substantially perpendicular to a central axis of the vessel.

The phrase "Framingham risk factor" as used herein refers to any condition that increases the Framingham Risk Score as established by the Framingham Heart Study. For example, smoking or an HDL cholesterol level lower than 40 results in an increased Framingham Risk Score. The criteria for Framingham risk factors related to total cholesterol and systolic blood pressure vary based on age and gender.

As used in the specification and claims, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

Unless specifically stated or obvious from context, as used herein, the term "or" is understood to be inclusive.

DETAILED DESCRIPTION

Imaging real-world vessels, whether biological, industrial, or otherwise, remains challenging because of the intrinsic noise and vessel motion caused by fluid flow and other sources. For example, imaging of the coronary artery is constrained by noise and motion caused by blood flow, heart rate, and breathing rate. Likewise, a high-pressure fluid line in an industrial plant is subject to pulsations, vibrations, and fluctuations in fluid pressure caused by pumps and other equipment. Just as it is not possible to pause a subject's heart in order to obtain a better image, it may also be impossible or expensive to take a piece of equipment offline in order to inspect tubing and other vessels.

Aspects of the present subject matter provided herein enable imaging of vessels by compensating for fluid flow (e.g., blood flow), internal motion (e.g., cardiac motion), and external motion (e.g., respiratory motion). Stated generally, aspects of the present subject matter utilize a cinematic approach to capture multiple images frames, thereby accommodating natural fluctuations. In biomedical applications, the present subject matter enables both the cinematic black blood imaging of a vessel as well as cinematic imaging of coronary vessels using phase-sensitive black blood techniques during free-breathing.

Assessment of Vascular Health Using Magnetic Resonance Imaging

Aspects of the present subject matter provide MRI methods for reliably imaging vascular wall thickness while the vessels can be subject to aperiodic intrinsic motions including, for example, cardiac and chest wall motions and blood flow motions, which degrade vessel image resolution. The present subject matter provides methods for assessing the health of the vascular system by using the MRI methods described herein.

Coronary artery wall assessment (as well as assessment of other vessel walls within the body) with MRI has great potential as a radiation-free method for coronary artery disease (CAD) assessment and for evaluating arterial wall remodeling that precedes lumen narrowing. The procedure can thereby provide further insight in the understanding of atherosclerosis and its response to various therapies. However, technical challenges still hinder coronary wall imaging for routine clinical utilization. These challenges include image degradation due to aperiodic intrinsic cardiac and chest wall motions. Residual motion due to uncompensated heart-rate variability, motion within the navigator gating window, or other bulk motion often cause image blur and reduced sharpness (8-10). These challenges are further complicated by the time-dependent angular orientation of the small caliber arterial wall, whereby mispositioning of the imaged slice can cause disappearance of the lumen-wall interface altogether (11-13). This can drastically reduce arterial wall imaging reliability and success rate. While the failure rate of coronary MR angiography (MRA) ranges from 10% to 20% of the imaged cases (8), this rate is more pronounced in MR coronary wall imaging, ranging from 26% to 33% (4, 7, 14).

Two-dimensional (2D) and three-dimensional (3D) coronary arterial wall imaging techniques have been proposed. Although 3D imaging provides larger volumetric coverage, it requires sophisticated planning for successful blood nulling and prohibitively prolonged scan times to achieve the necessary high resolution with a greater risk of degraded image quality (15). Therefore, the convenience of 2D coronary vessel wall imaging and its relatively faster imaging time compared to 3D has led to its widespread utilization in clinical studies (2, 7, 16).

In planning 2D coronary arterial wall imaging, the slice is prescribed orthogonal to the artery longitudinal view at the location of interest. Violation of this orthogonality is often encountered and dramatically alters the perceived wall and lumen dimensions. It can also cause the failure to resolve the wall altogether (11, 13). This orthogonality is crucial for obtaining an accurate measurement of wall thickness. However while imaging at only the blood-signal nulling time, it is difficult to maintain slice—vessel orthogonality as this condition is highly sensitive to any cardiac rhythm variation or unaccounted bulk displacement. Previously proposed solutions, including vessel tracking (17-21), subject-specific acquisition windows (22), and adaptive trigger delays (23-25), cannot guarantee preservation of the orthogonality required for optimal 2-D wall imaging and accurate quantitative assessment.

Another challenge facing successful vessel wall imaging is the lack of robust blood nulling. A phase-sensitive dual-inversion recovery (PS-DIR) black-blood imaging technique (26) has been recently developed to address this challenge. PS-DIR relaxes the constraints related to blood-signal nulling time and the period of minimal myocardial motion and thus enables black-blood imaging to be less sensitive to imaging time parameters. The present subject matter provides methods wherein multiple coronary wall PS-DIR images can be acquired sequentially. In one embodiment, the present subject matter provides an improved method for obtaining the required orthogonal view of a vessel in one of the sequential time-resolved images as compared to a single image acquisition methods of existing imaging techniques. Consequently, time-resolved PS-DIR vessel wall imaging of the present subject matter can: (1) improve the success rate of coronary vessel wall imaging and (2) provide a more accurate view of wall thickness and precise differentiation between normal and diseased wall-thickened states.

The present subject matter provides a time-resolved PS-DIR coronary vessel wall MRI technique that overcomes the loss of the orthogonality due to uncompensated residual motions.

Magnetic Resonance Imaging Devices

Referring now to FIG. 1, an exemplary magnetic resonance imaging (MRI) device [101] is depicted. The MRI device [101] includes a scanner housing with a magnet having a typical magnetic field ($B_0$), ranging from about 0.5 to about 7 Tesla or higher, positioned inside the housing. When the subject to be imaged, for example a human body lying on the scanner table [102], is disposed within the bore of the MRI equipment, the hydrogen and other nuclei in the subject are realigned in certain directions. Magnetic field gradient coils [103] are arranged near the imaged subject to superimpose on $B_0$ an additional selected spatially-varying magnetic field. One or more radiofrequency (RF) coils [108] are arranged inside the bore of the magnet to transmit RF excitation and inversion pulses ($B_1$). The RF coils [108] also measure the RF magnetic resonance signal emitted from the imaged subject. (Some RF coils can be used to both transmit and receive RF signals, while other RF coils are use to only transmit or receive signals. The work done in this study utilized separate coils to transmit and receive RF signals. However, concepts discussed here can be applied on any type of coils.) The gradient coils [103] and the RF transmitter coils [108] are turned on and off at specific strengths and for specific duration according in a predetermined sequence of actions collectively called an imaging sequence implemented by an imaging sequence controller [106]. At specific time points during the execution of the imaging sequence, the RF receiver coils [108] measure the RF signals emitted from the body [102]. Images of body parts or organs are created from the measured RF signals during or after the completion of the imaging sequence by the cine image reconstruction module [111].

The MRI device [101] can include one or more modules programmed to control the operation of the MRI device [101]. For example, an image sequence memory module [105] can store one or more imaging sequence algorithms that specify the relative timing on one or more RF pulses and/or image captures. Such imaging sequences can be specified with respect to cardiac cycle signal so that the imaging will occur when the vessel is in a relatively quiescent state. Such imaging sequences can be variable with respect to parameters such as a trigger delay and an inversion delay as further discussed herein.

The imaging sequence controller [106] can obtain one or more image sequence algorithms from the imaging sequence memory and control one or more of a magnetic field gradient controller module [104], a radio frequency (RF) pulse controller module [107], an analog/digital (A/D) signal converter module [110], and the cine image reconstruction module [111] in order to effect the application of RF pulses and/or image capture.

The cine image reconstruction module [111] can communicate with the analog/digital (A/D) signal converter module [110] to receive digital images of the subject. The cine image reconstruction module can store these images in an image memory module [126], image storage module [112], and/or image processing memory module [113]. Phase-sensitive reconstruction module [114] and/or wall thickness calculation module [115] can communication with image processing memory module [113] to obtain one or more images for further analysis as discussed herein.

As will be appreciated by one of ordinary skill in the art, the various modules described herein can be distinct hardware and/or software modules or can be combined into one or more hardware and/or software modules. For example, the magnetic field gradient controller module [104], radio frequency (RF) pulse controller module [107], and analog/digital (A/D) signal converter module [110] can be interfaces provided and incorporated within the MRI device [101] while the imaging sequence controller [106] is external to the MRI device [101]. Alternatively, the imaging sequence controller [106] can be incorporated within the MRI device [101].

Imaging Sequences

Figure 4:
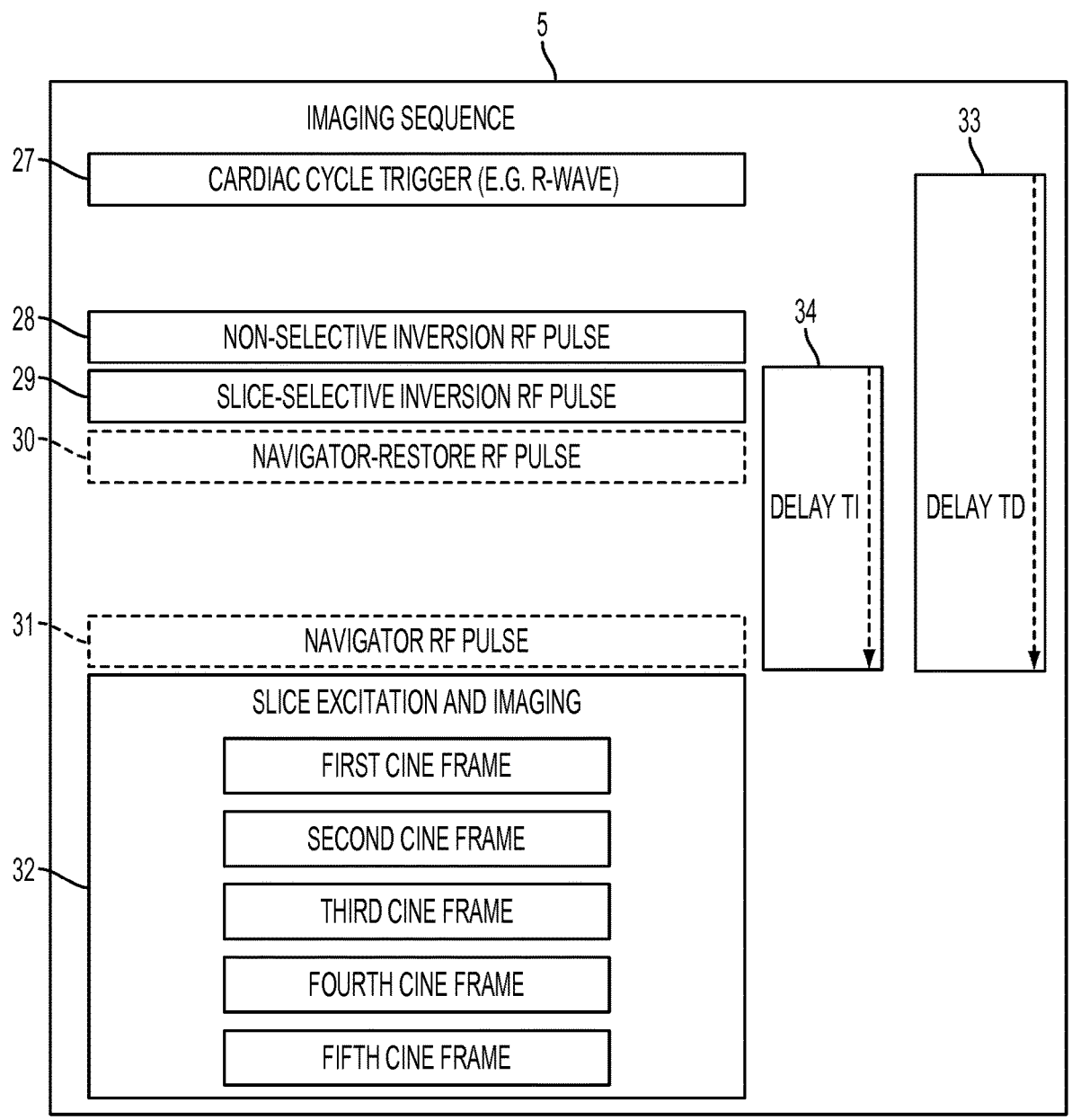
FIG. 4 depicts a schematic diagram of one example of an imaging sequence for use with the TRAPD method according to the present subject matter. Multiple vessel wall images are acquired consecutively. The acquired images are processed by methods as in the examples in FIG. 3 and FIG. 4 to correct for the potential modulus magnitude artifacts inside the vessel lumen and other motion-related artifacts in order to reliably measure an estimate of vessel wall thickness.
Figure 5:
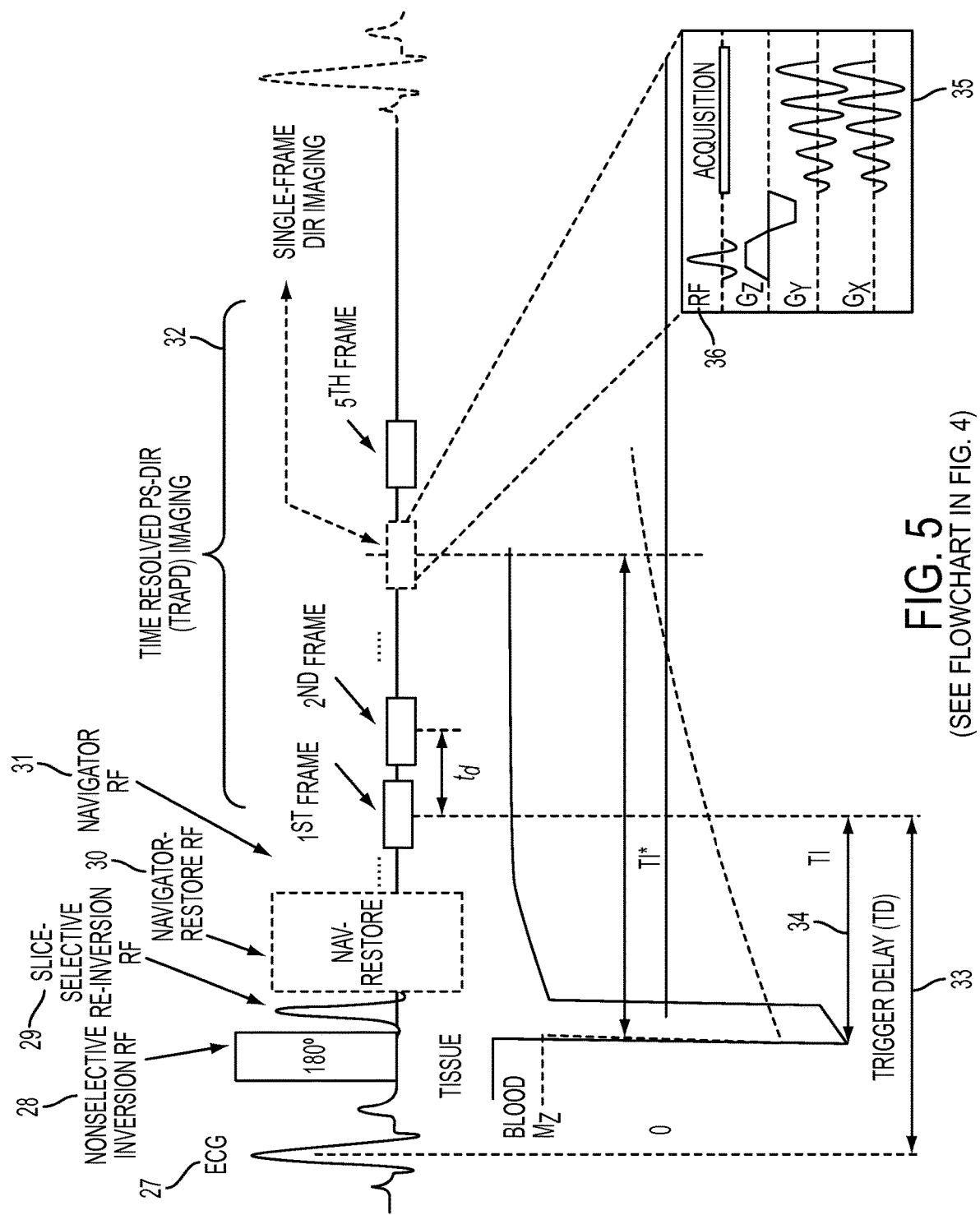
FIG. 5 depicts a schematic timing diagram of one example of a time sequence of the TRAPD method according to the present subject matter Timing of conventional dual-inversion recovery (DIR) sequences, TRAPD pulse sequences, and cinematic image acquisition are shown. DIR images are acquired at TI* when blood magnetization is nulled. In TRAPD, time-resolved multiple frame acquisition starts at earlier time point TI<TI*. Post-processing can be utilized as in the examples shown in FIG. 3 and FIG. 4 to suppress lumen blood signal artifacts and to enhance the lumen-wall signal contrast.

Referring now to FIGS. 4 and 5, various aspects of the present subject matter utilize imaging sequences that capture a plurality of cine images of a slices of interest over a period of time. Such imaging sequences can advantageously incorporate phase-sensitive dual-inversion MRI techniques as will be described below.

The imaging sequence [405] is specified relative to a cardiac cycle trigger (e.g., an R-wave obtained from an electrocardiogram device).

A trigger delay (TD) [433] specifies an expected time period between the cardiac cycle trigger and a period when the vessel will be in a quiescent state. Appropriate TD values vary based on the subject's heart rate and can be calculated manually or automatically by existing MRI devices. Appropriate TD values from the R-wave to any time during the systole period are between about 10 ms (i.e., directly after the R-wave and any preparation pulses) and about 5 s.

In step [428], a non-selective inversion RF pulse is applied to the region of interest in order to invert all spin magnetizations. Next, in step [430] a slice-selective inversion RF pulse is applied to the slice of interest. This slice-selective inversion RF pulse has the effect of returning the magnetization of the slice to its original non-inverted state. However, as fluid flows through the vessel, incoming fluid that was outside of the slice-selective inversion RF pulse in step [430] will be inverted.

In order to allow for this inverted fluid to enter the portion of the vessel within the slice of interest, imaging is delayed by an inversion delay (TI) [434] that varies based on the subject's heart rate. As with the trigger delay (TD), the inversion delay (TI) [434] can be set manually or automatically be existing MRI devices. Ranges of appropriate TD values relative to the R-wave are between about 20 ms and 500 ms.

If the sequence runs in free-breathing navigator-guided mode, an optional navigator pulse [431] is applied directly before imaging [432] to track and compensate for lung motion. Combined with the navigator pulse [431], a navigator-restore pulse [430] can be used to re-invert magnetization at the anatomical location monitored by the navigator mode. If the sequence is to be executed in breath-hold mode or in free-breathing mode when breathing motion does not displace the vessel of interest, no navigator pulse is required.

After the trigger delay and the inversion delay elapse, imaging commences. Unlike conventional imaging techniques that attempt to capture a single image at point TI=TI* (depicted in FIG. 5) when the polarity of the blood is 0 (or nulled) or the phase-sensitive black-blood technique taught by (26) that relaxes the required timing for capturing the single image to TI<TI*, aspects of the present subject matter capture a plurality of cine images in step [432] in order to maximize the likelihood that one or more of the cine images will be of sufficient quality for further analysis.

The number of cine images can vary depending on the temporal resolution of the MRI device [101] (i.e., how quickly the MRI device can capture consecutive images), the expected duration of the quiescent period of the vessel, and memory and processing considerations. In one embodiment, five cine images are captured at 25 ms intervals after a 150 ms inversion delay (TI). Although a uniform interval between cine images may be preferred in many embodiments, the delay can be non-uniform.

The imaging sequence can be repeated periodically to gather a plurality of cine images (e.g., of the same slice or of difference slices). For example, the imaging sequence can be performed every, every other, every third, or every n-th cardiac cycle (where n is a positive integer). The images slices can be a two-dimensional place or a three-dimensional volume.

Time-Resolved Acquisition of PS-DIR (TRAPD)

As discussed above, FIG. 5 depicts a non-selective inversion radiofrequency pulse directly followed by a slice-selective re-inversion of the magnetization at the anatomic level of interest. This dual-prepulse maintains the original magnetization at the excited level while the inverted magnetization of the in-flowing blood is nulled at a specific nulling time TI* (27). The absence of the MR signal polarity, i.e., the positive and negative signs, in typical DIR black-blood images can result in a suboptimal blood-tissue contrast if the imaging time TI≠TI* (26, 28).

Figure 2:
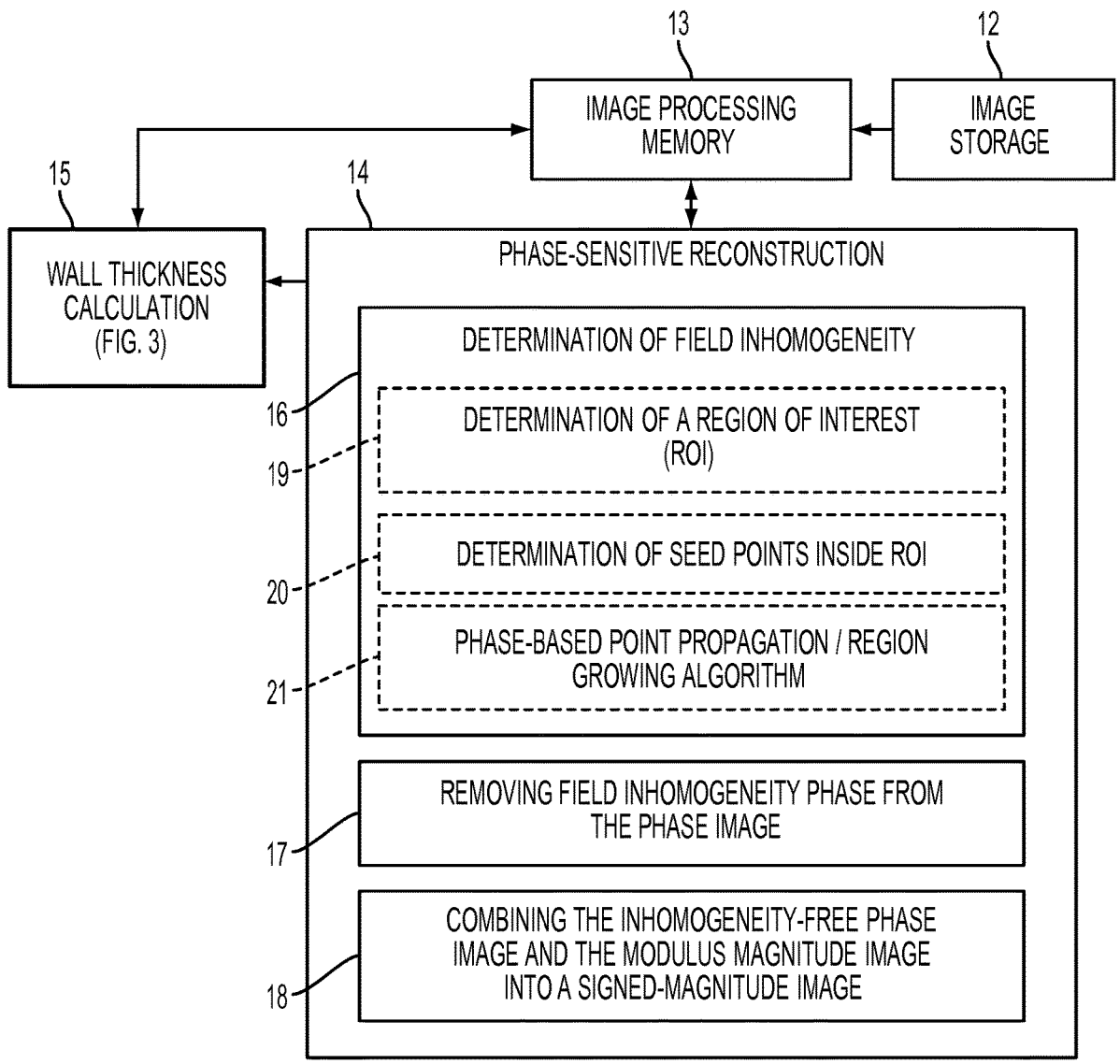
FIG. 2 depicts a schematic diagram of one example of a method for conducting phase-sensitive reconstruction according to the present subject matter. The local magnetic inhomogeneity phase map is evaluated locally in and around the vessel lumen based on a semi-automatic local region-growing algorithm comprising the listed steps.

Phase-sensitive DIR (PS-DIR) reconstruction of coronary black-blood images (26) alleviates these stringent requirements for the timing of black-blood MRI and the sensitivity of lumen-tissue contrast to imaging time TI. To reduce the adverse effects of intrinsic myocardial motion, the period of minimal myocardial motion can be visually inspected on a transaxial cine scan (29), the depicted time of cardiac rest period (TD) [433][533] is then used for coronary artery imaging (30, 31). Oftentimes, however, heart rate changes and bulk motion occurs due to the extended stay inside the scanner. In addition, rest periods vary in time and duration with heart rate and from one arterial segment to another while over one-third of the segments have no rest periods (32, 33). These uncertainties can largely and conveniently be overcome by embodiments of the present subject matter if black-blood imaging is enabled at several time-points throughout the formerly determined cardiac rest period. The PS-DIR sequence can be modified in an embodiment of the present subject matter to acquire several successive frames. In one embodiment of this time-resolved acquisition of PS-DIR (TRAPD) approach, each frame is reconstructed into a PS-DIR sign-preserved magnitude image (26) as depicted in FIG. 2. The cine sequential time-resolved images can trap the changes in coronary wall position and angulations during the rest period, which can then permit more accurate selection of the image with optimal position, angulations and hence potential for accurate measurements.

The information about the vessel wall in these multiple acquired images are used to obtain a more robust estimate of vessel wall thickness than the estimate obtained from a single image. Utilization of such information can have several forms. Non-limiting examples of such utilization are depicted and described in the context of FIGS. 2 and 3, in which the optimal vessel wall thickness is determined as the smallest of all the measurements. Other scenarios for determining the most accurate wall thickness can consider more sophisticated strategies like lumen area and shape, wall area and shape, or other features.

Phase-Sensitive Dual-Inversion Reconstruction

Referring now to FIG. 1, an exemplary method for Phase-Sensitive Dual-Inversion Reconstruction (PS-DIR) [214] is provided.

Determination of Field Inhomogeneity Phase

A local magnetic inhomogeneity phase map is evaluated locally [216] in and around the vessel lumen based on a semi-automatic local region-growing algorithm with the following actions.

In step [219], the user digitally selects a pixel near the center of the lumen of an imaged vessel. The image can be from any source, including, for example, image storage [212] or image processing memory [213]. A ring-shaped region-of-interest (ROI) is chosen to cover a large area of the surrounding tissue (e.g., myocardium) in close proximity to the cross-sectional vessel (e.g., coronary artery.)

In step [220], pixels with high magnitude signal intensity (for example, those with intensity in the top 85 percentile in the intensity or SNR histogram of all the points in the ROI) within the myocardium in that region are pooled. Given this selection criterion, the phase values of these pixels are expected to be least distorted by noise and are representative of the corresponding locations.

In step [221], the pooled phase values from [220] serve a seed points for a phase region-growing algorithm in order to increase the population in the pixel-pool of around the arterial wall. The developed phase region-growing algorithm is similar to that proposed by Szumowski et al. ("Phase unwrapping in the three-point Dixon method for fat suppression MR imaging." Radiology 192(2):555-561 (1994)), but is restricted to run within the ring-shape ROI. Bilinear interpolation is then applied to estimate the inhomogeneity phase in and around the coronary vessel. Inhomogeneities mapped out with this method might arise from a variety of sources, including, for example, magnetic field susceptibility, $B_0$ and $B_1$ inhomogeneity, non-uniform coil sensitivity, imperfect gradients, and eddy currents.

Removing Field Inhomogeneity Phase from the Phase Image

Given the estimated field inhomogeneity phase calculated from [220], an inhomogeneity-free phase image can be created in step [217] by removing the field inhomogeneity phase from the phase image through angular subtraction as discussed in (26). Thus, the sources of such inhomogeneities are controlled for and their affects are minimized in the phase images to be further analyzed.

Creating a Signed-Magnitude Image

In step [218], a signed-magnitude image inside and around the vessel can be created by combining the inhomogeneity-free phase image and the modulus magnitude image into a signed-magnitude image by multiplying the modulus magnitude image and the cosine of the inhomogeneity-free phase image on a pixel-by-pixel basis as discussed in (26). The reconstructed signed-magnitude image can then be further analyzed for vessel wall thickness measurements by the wall thickness calculating method [215] and/or stored in image memory for later analysis [213].

Quantifying Vessel Wall Thickness

Figure 3:
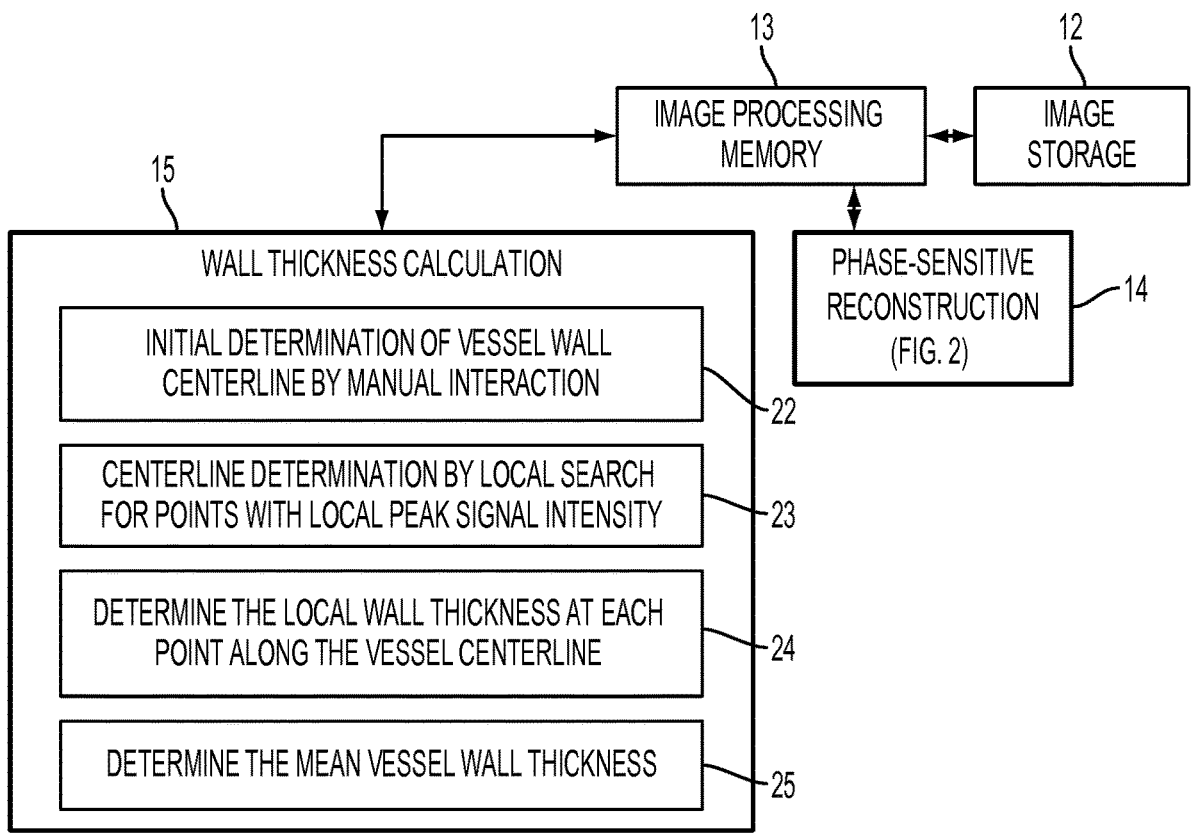
FIG. 3 depicts a schematic diagram of one example of a method for analyzing and measuring vessel wall thickness from the images depicting vessel walls according to the present subject matter.

Referring now to FIG. 3, another aspect of the present subject matter provides a method for quantifying vessel wall thickness [315]. After Phase-Sensitive reconstruction in module [214] (depicted and described in the context of FIG. 2), a semi-automatic algorithm for wall thickness measurement can perform wall thickness measurements.

In step [322] images were zoomed to about 500% and the user localized the vessel wall by manually tracing 15 to 25 pixels along an initial centerline of the vessel wall. In step [323], the pixels with peak-intensity value in a 3×3 point neighborhood of each of the manually traced points were automatically identified and these points represented a more accurate centerline of the vessel wall. In step [324], the direction of maximum intensity variation was identified automatically at each point along the centerline. Subsequently at each point, a one-dimensional distribution-shape model (e.g., Gaussian or other shape model) was automatically fit across the wall along the direction of maximum intensity variation. The outer (adventitial) and inner (luminal) boundaries of the coronary wall were automatically identified as the two points of steepest gradients on the sides of each of the distribution (e.g., Gaussian) shapes. In step [325], vessel wall thickness (e.g., coronary artery wall thickness) in each image was measured as the average distance between the previously identified inner and outer boundaries.

Working Example 1

Implementation of TRAPD in a Variety of Exemplary Controls and Samples

In one example of the present subject matter, the TRAPD sequence depicted and described in the context of FIG. 5 was implemented on a commercial human 3T MRI system (sold under the ACHIEVA™ mark by Philips Medical Systems of Best, the Netherlands). Data were acquired using a segmented k-space spiral acquisition with spectral spatial water-selective excitation (34), using a 32-channel phased array cardiac receiver coil and vector ECG triggering (35). Data from the 16 anterior surface coils were used for image reconstruction. A series of phantom and in vivo experiments were conducted. Image processing was performed off-line using a custom-built software tool developed using MAT-LAB® ver. 7.8 (Mathworks, Natick, Mass.) with similar functionalities to previously published tools (4, 36).

Phantom Setup

For proof of concept, one example of a flow-phantom of the present subject matter was built similar to the one in (26) using a plastic (PVC) 200 mm long tube with a lumen-diameter of 3.2 mm and a wall-thickness of 1.6 mm. The tube was embedded in agarose gel ($T_1$=1200 ms) and was positioned in the iso-center of the magnet and in parallel to the main magnetic field. Tap water ($T_1$=3200 ms) was flowing at a constant velocity of 25 cm/s.

Imaging Protocol

A series of 10 consecutive TRAPD images of a transaxial slice perpendicular to the tube was acquired with incremental inversion times (TI=25, 100, 150, . . . , 250 ms). The spiral readout consisted of 22 interleaves using an RF excitation angle $\alpha$=45° and an acquisition window of 18 ms for each. The spatial resolution was 0.66×0.66×8 0 $mm^3$ (FOV=200×200×8 $mm^3$, matrix=288×288). The re-inversion slab thickness was 15 mm. A simulated R-wave was generated every second (TR=1000 ms) and the total scan time was 22 s. All the data were reconstructed with both the conventional DIR and the PS-DIR reconstruction algorithms (26).

Data Analysis

Two 3×3-pixel regions of interest (ROI) positioned in the lumen and in the agarose gel, respectively. The average signal intensities were then computed for both ROIs ($S_{Lumen}$, $S_{Background}$). In all the DIR and PS-DIR images, the contrast was defined as $[(S_{Background})-(S_{Lumen})]/(S_{Background})$.

Working Example 2

In Vivo Experiments: Subjects

Twenty six subjects with at least one Framingham CAD risk factors and 12 healthy subjects without history or risk factors for CAD (<1% Framingham score) were scanned in the supine position. Ages, BMI, and other population characteristics are displayed in Table 1.

TABLE 1

Study population characteristics.

|  | Patients | Normal | P-value |
|---|---|---|---|
| Number (total, males, black) | 26, 13, 11 | 12, 3, 1 |  |
| Age (mean ± SD, min., max.) | 48 ± 18, 18, 75 | 26 ± 4, 23, 32 | <0.001 |
| BMI (mean ± SD, min., max.) | 25 ± 5, 16, 34 | 22 ± 4, 20, 30 | 0.062 |
| Hypertension (n) | 9 |  |  |
| Smoking (n) | 4 |  |  |
| HDL (n) | 14 |  |  |
| A1C (n) | 2 |  |  |

Scout Scanning

Localization of the heart and the right coronary artery (RCA) tree was planned similar to previously published methodologies (1, 37). A free-breathing axial VCG-triggered, steady-state free precession cine image series (TE/TR/$\alpha$=1.8 ms/3.8 ms/45°, and a temporal resolution of 39.6 ms) at the level of the proximal to mid right coronary artery (RCA) was obtained. The patient-specific time-delay between the R-wave of the ECG and the diastolic rest period (TD) was visually identified from the cine image and used for the subsequent coronary MRA and wall imaging.

Coronary MRA

Volume-targeted navigator-gated 3D segmented k-space gradient echo coronary MRA was acquired using the previously identified TD. The coronary MRA was oriented in parallel to the major axes of the right coronary arterial (RCA) system with TE/TR/$\alpha$=2.1 ms/8 ms/20°, FOV=270× 270×3 $mm^3$, matrix=384×268, and acquired voxel dimension of 0.7×1×3 $mm^3$ Real-time navigator respiratory gating (5 mm gating window, slice tracking) was used (38, 39).

Imaging Protocol

Single-slice TRAPD coronary vessel wall datasets were acquired. Depending on heart rate and the starting point of the rest period, 4 or 5 time frames were acquired in each cine dataset using a fixed imaging time TI=200 ms for the first image and a temporal resolution Tr=25 ms between subsequent frames. The spiral readout consisted of 20 interleaves with a flat flip angle $\alpha$=45°, an acquisition window of 20 ms, TE/TR=2.1 ms/1 RR interval, and the spatial resolution was 0.69×0.69×8.0 $mm^3$ (FOV=200×200×8 $mm^3$, matrix=288× 288). The re-inversion slice thickness of 15 mm was used to accommodate for potential spatial mis-registration between the magnetization-prepared slab and the imaged slice due to through-plane cardiac motion. Data were acquired using prospective navigator gating and correction (39). The navigator was localized at the lung-liver interface of the right hemi-diaphragm with a 3 mm gating window and a correction factor of 0.6 in superior-inferior direction (40) Immediately after dual-inversion, a navigator restore pulse (41) was used to optimize navigator performance. Phase-sensitive signed-magnitude images were reconstructed (26) and used in all later analyses.

Data Analysis

All cine images in this example were randomized, anonymized, and evaluated for the image quality. Two observers scored the visual quality of the vessel wall by consensus. A score from 0-5, using criteria as previously described (42), was assigned to each image. A score of 0 indicated the image was not acquired due to short cardiac cycle; a score of 1 indicated an undistinguishable coronary wall (very poor quality); a score of 2 indicated the coronary artery wall partly visible (<50%) with incomplete borders (poor quality); 3, where 50%-75% of the coronary artery wall is visible and distinguishable from the lumen and surroundings (fair quality); 4, where the coronary artery wall is mostly distinguishable with only small portions of the vessels (<25%) were not present (good quality); and 5, where the coronary artery wall is completely visible with sharply defined borders (excellent quality). An image with a good or excellent quality was considered adequate for quantitative analysis. These images were all pooled and analyzed, blinded to subject information.

Coronary Wall Measurement

Images were zoomed to 500% and the user localized the vessel wall by manually tracing 15 to 25 points along an initial centerline of the vessel wall. The points with peak-intensity value in a 3×3 point neighborhood of each of the manually traced points were automatically identified and these points represented a more accurate centerline of the vessel wall. The direction of maximum intensity variation was identified automatically at each point along the centerline. Subsequently at each point, a one-dimensional Gaussian-shape model was automatically fit across the wall along the direction of maximum intensity variation. The outer (adventitial) and inner (luminal) boundaries of the coronary wall were automatically identified as the two points of steepest gradients on the sides of each of the Gaussian shapes. Coronary artery wall thickness in each image was measured as the average distance between the previously identified inner and outer boundaries.

Lumen-tissue contrast-to-noise ratio (CNR) was calculated on the PS-DIR signed-magnitude images using the formula $CNR=(M_{wall}-M_{blood})/SD_{noise}$, where mean signal intensity $M_{blood}$ in the center of the lumen was calculated, mean vessel wall signal $M_{wall}$ was calculated from inside the vessel wall, and noise standard deviation $SD_{noise}$ was calculated inside the lung in a structure-free region. The vessel wall edge definition or sharpness was also measured similar to that reported in (36).

To assess the potential benefits of the additional TRAPD cine frames in the present example, in each dataset, the time-frame with minimum vessel wall thickness was identified and considered the most accurate measurement of wall thickness. In addition, to study the incremental value of each additional time-frame in this example, the minimum vessel wall thickness was identified considering the acquisition of only the first two, three, four, and five frames and these were compared pair-wise and to the wall thickness measured in the first frame as representative of the conventional single frame approach. In each population, Friedman repeated measures ANOVA and trend analysis tests were utilized to examine the equality of the thickness measurements obtained with single frame images and those minima incorporating the additional time-frames, and to identify the number of frames with significant influence on minimum wall thickness measurement. Mann-Whitney test was used to compare wall thickness measurements between normals and CAD-risk subjects. Between-group wall thickness difference was also compared using pair-wise t-tests. MED-CALC® version 11.6 software (available from MedCalc Software of Mariakerke, Belgium) was used for all statistical analyses. A Bonferroni-corrected p value of <0.05 was considered to be statistically significant.

Reproducibility

For intraobserver and interobserver reproducibility, all image processing and wall thickness measurements for this example were repeated by the first and second observers for 20 randomly selected subjects. The first measurement performed by observer 1 is considered the reference standard. Additionally, to assess the interscan reproducibility, additional sets of TRAPD images were acquired from 18 subjects during the same session and of the same coronary segments. Images underwent the same blind procedures done for the original datasets including analysis, and wall thickness measurements. Data from the different measurements and different scans were compared using paired t-test. Intraobserver, interobserver, and interscan correlations were evaluated using the Pearson correlation coefficient (R). The Bland-Atlman method was used to study systematic differences (44). The intraclass correlation coefficient (ICC) for absolute agreement was calculated to assess intraobserver, interobserver, and interscan agreements. The coefficient of variance (CoV) and the concordance correlation coefficient (CoC) were also determined. The CoV (%) was defined as the standard deviation (SD) of the differences between the two measurements divided by the mean of both measurements (100×SD/mean). The CoC (45) evaluates the degree to which pairs of measurements fall on the 45° line through the origin.

Results

Phantom Experiment

Figure 6:
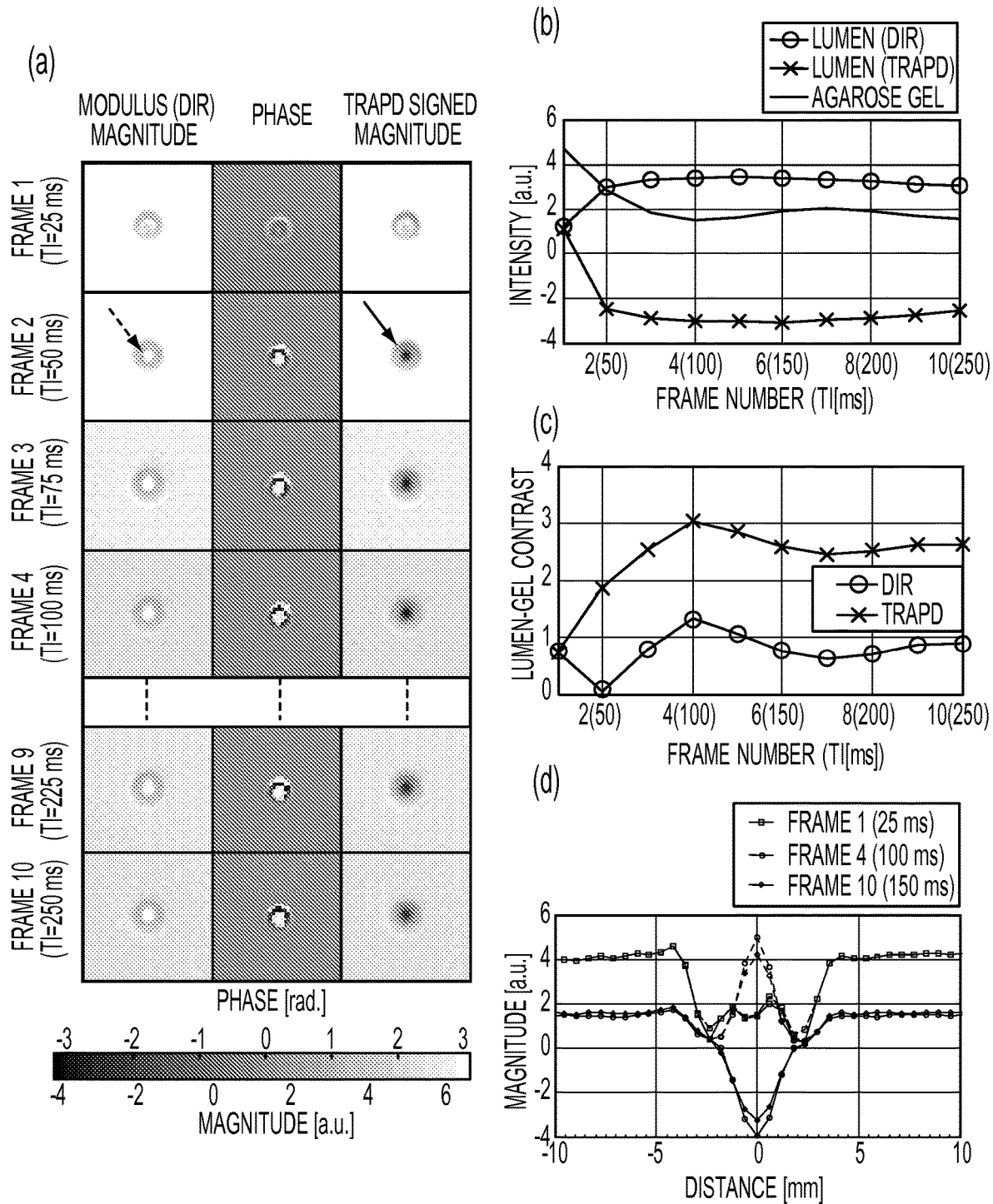
FIGS. 6(a)-(d) show examples of TRAPD Phantom signal intensity and lumen-wall contrast using incremental TI ranging from 25 ms to 250 ms.

TRAPD magnitude and phase data for this example are shown in the first and second columns of FIG. 6(a), respectively. Successful restoration of signal negative polarity inside the lumen along multiple frames is demonstrated in the signed-magnitude images of FIG. 6(a) (third column, solid arrow), compared to modulus-magnitude DIR images (left column, dashed arrow). Time profiles of modulus and TRAPD signed signal intensities are shown in FIG. 6(b). The progressive reduction in agarose signal intensity demonstrates the effect of recurring excitations on stationary tissues. Starting from TI=50 ms and later inside the lumen, fluid with inverted signal moved into the slice and replaced the original fluid. This behavior was correctly interpreted with phase-sensitive reconstruction. Lumen-gel contrast profile, as displayed in FIG. 6(c), further demonstrates the persistent higher contrast with TRAPD reconstruction in comparison with the limited irregular DIR contrast pattern. These intensity temporal changes are further quantitatively demonstrated in the time-resolved cross-sectional signal intensity profiles shown in FIG. 6(d). The curve at "TI=25 ms" shows the highest tissue signal intensity which gradually reached a reduced intensity plateau with sequential imaging. However, since the fluid initially inside the lumen was quickly replaced by out-of-plane fluid with inverted spins, the tissue-lumen contrast improves at TI=100 ms with a signal difference that is almost three times greater.

In Vivo Experiments

Figure 7:
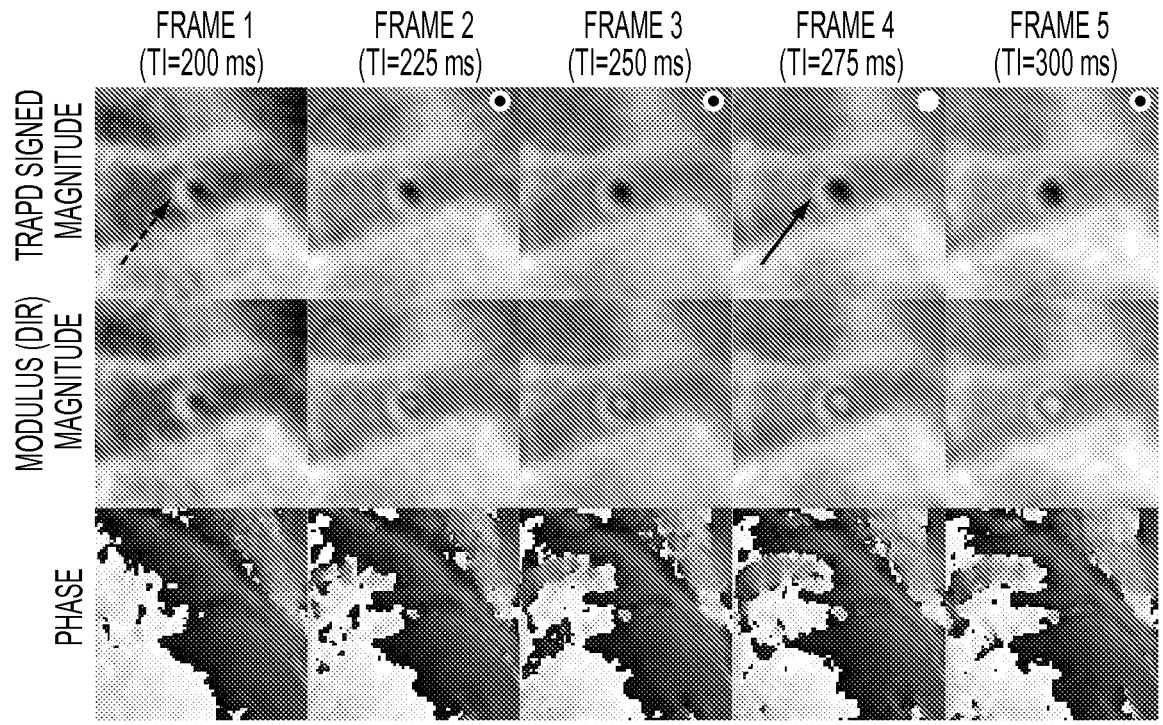
FIG. 7(a) depicts examples of (a) TRAPD (top row) and conventional DIR images (second row) of a healthy subject. White circles denote the frames with good or excellent quality. Filled circle denotes the frame with the thinnest wall thickness measurement.
FIG. 7(b) depicts line intensity profiles across the coronary vessel wall and lumen at different time frames using TRAPD (solid lines) and DIR (broken lines). Data are from a subject without risk factors, whose heart rate during the scan was 63 beats per minutes, age 24 y.o., and BMI 26.
Figure 7:
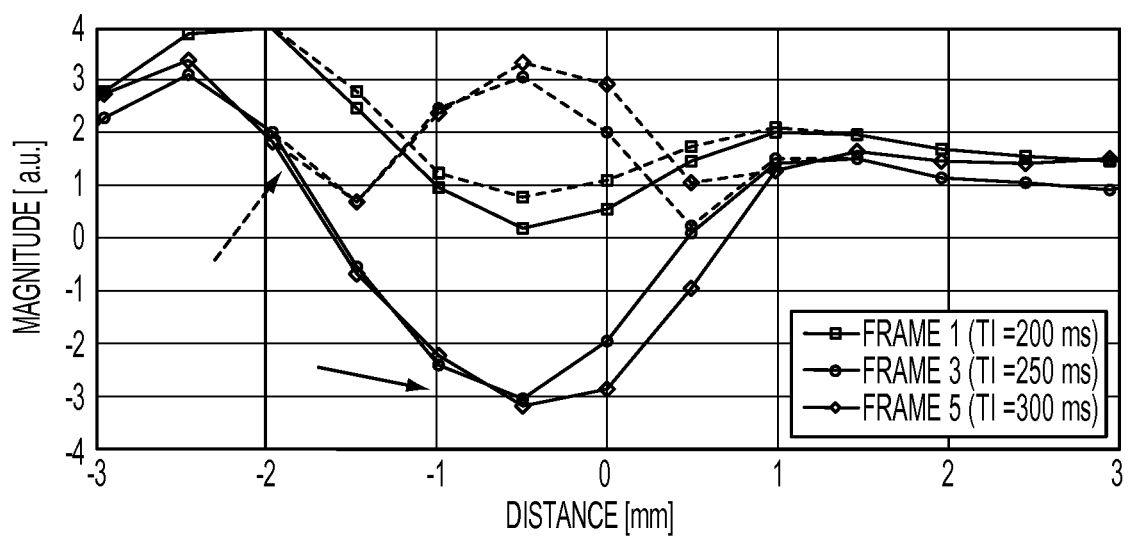

All 38 subjects were successfully imaged in this example. All datasets except two had at least one time-frame image with good or higher quality scores. An example TRAPD dataset from a healthy subject is shown in FIG. 7. In that figure, white circles denote images with good or excellent quality scores and filled circles denote the images with the thinnest vessel walls.

Minimum motion trigger delay time TD was always determined from an earlier cine acquisition to visually identify diastole, as proposed by previous studies. Nevertheless, the effects of unpredicted through-plane motion and loss of orthogonality positioning are shown in the first frame in FIG. 7, demonstrated as incomplete vessel wall and elongated lumen shape (dashed arrows). The artery gradually changed its orientation and lumen and wall shape roundedness was achieved when the artery longitudinal axis becomes orthogonal to the imaged slice. This condition was reached at late frames (solid arrows) in FIG. 7 where minimum wall thicknesses were also quantitatively identified.

FIG. 7(b) shows horizontal cross section intensity lines through the middle of the lumens clearly demonstrating the extent of lumen signal polarity correction (solid arrows) using phase-sensitive reconstruction. In neither case and at none of the frames, was an image acquired at the actual blood signal intensity null point. In fact, the temporal change of lumen signal intensity did not follow a specific pattern. In the case shown in FIG. 7(b), lumen signal intensity kept decreasing until the last frame. Neither the minimum wall thickness nor the widest lumen area was associated with a specific time frame. Although in FIG. 7(b), the fifth frame had maximum negative lumen signal intensity (solid arrow), the widest lumen and thinnest wall were measured at the fourth frame. This example illustrates the considerable subject-to-subject variability in the optimal imaging time point within the ~150 ms diastolic window.

Figure 8:
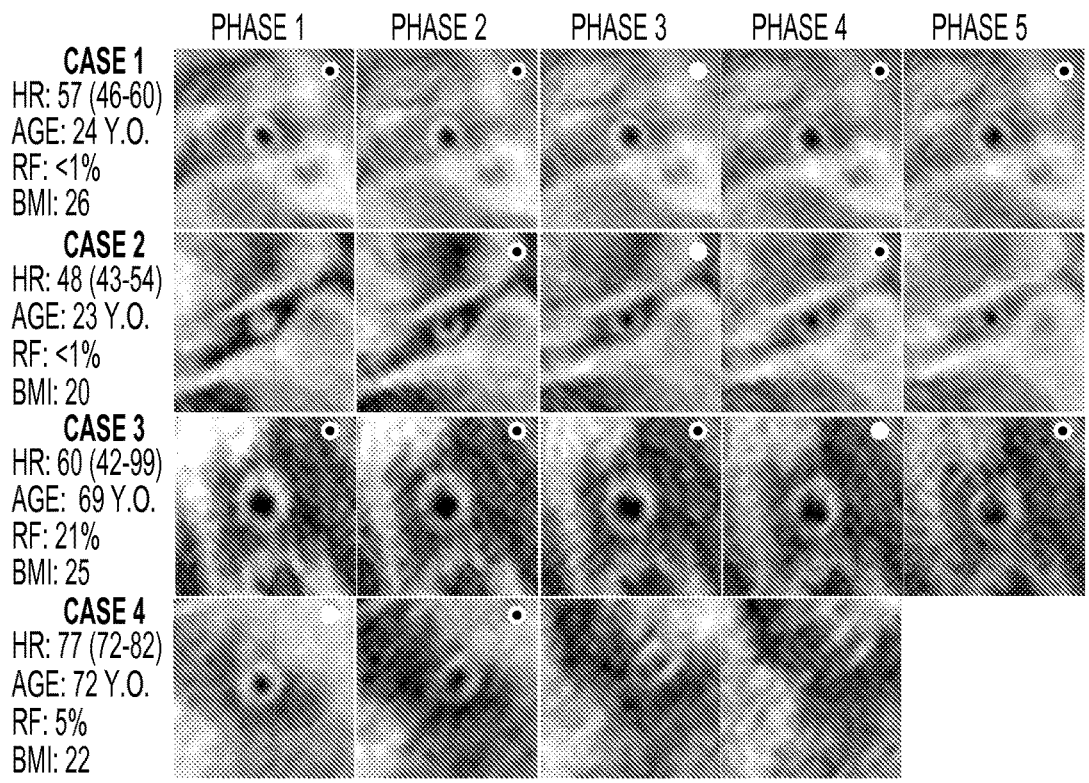
FIG. 8 provides examples of TRAPD signed-magnitude images of four different subjects demonstrating subject variability encountered in the study. Case 1 and 2 depict normal subjects. The other cases depict subjects with coronary artery disease (CAD) risk factors. The label beside each case shows the average, minimum, and maximum heart rate (HR) in beats per minutes during the scan, age in years, Framingham risk factor (RF), and BMI.

FIG. 8 summarizes the TRAPD reconstruction results from four other cases, representing the range of image qualities and demonstrating the variety of situations encountered during the study illustrating the extent of subject variability. Neither the thinnest vessel walls nor the good and excellent quality scores were exclusively associated with a particular frame. Cases 1 and 3 demonstrate the situations when all images had adequate (good or excellent) quality scores for quantitative analysis. In-plane and through-plane motions are evident in the others with various effects. Coronary wall and slice orthogonality can be achieved in the first frames, as in case 1 and 8, or in the middle frames, as in case 2. Case 4 is an example of short cardiac cycles in which it was impossible to acquire the fifth frames. Case 4 also shows a situation where only the first two frames had acceptable quality.

Success Rate and Image Quality

Figure 9:
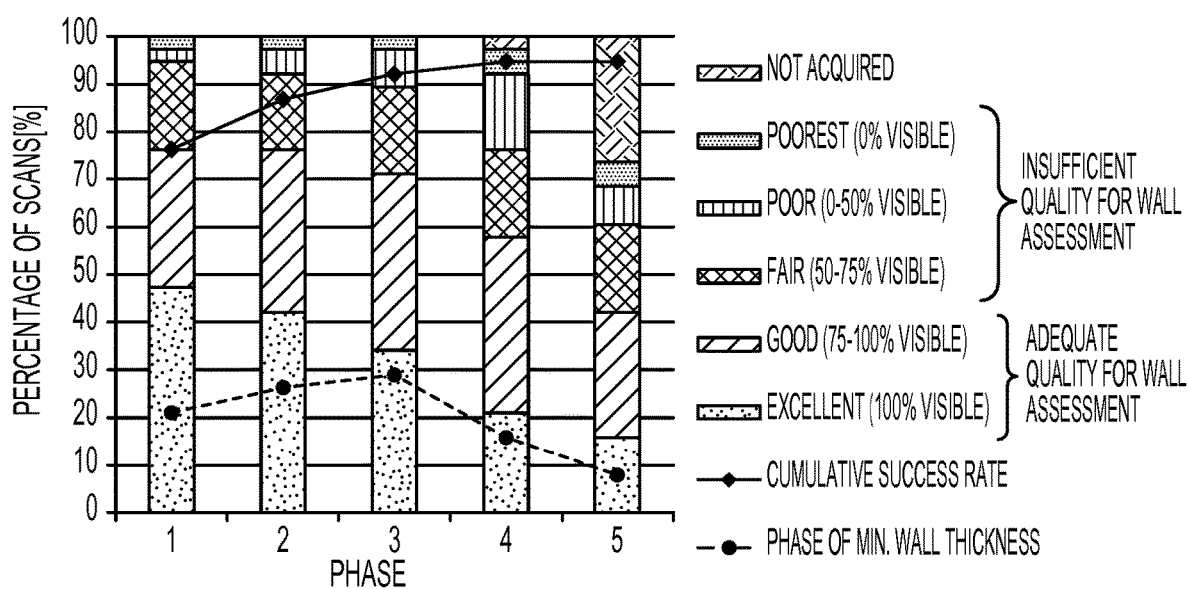
FIG. 9 provides bar graphs showing examples of distribution of image quality scores of each cine frame acquired. The solid curve depicts the cumulative success rate of obtaining images of good to excellent quality vs. the number of acquired frames. The dash lined curve depicts the percentage of scans with minimum wall thickness identified in the different phases.

The overall distribution of image scores over the cine frames is summarized in FIG. 9. In all subjects, the duration from TD to the next R-wave was long enough to acquire at least three TRAPD images. The duration was long enough to acquire four and five frames in 97% and 73% of the subjects, respectively. The first image frame had adequate quality in only 76% of the cases, which is in the range of success reported in previous single DIR imaging studies (4, 7, 14). The success of collecting adequate quality images in the second, third, fourth, fifth frames were 76%, 69%, 59%, 41% of the cases, respectively. As expected, highest success rate was associated with the images close in time to the predetermined TD value and were most likely acquired during the rest period. The later frames were more likely outside of the rest period and suffered in general from through-plane motion and image quality loss. Nevertheless, the acquisition and utilization of the additional frames increased the cumulative success rate of acquiring at least one adequate-quality image from 76% in single-image acquisitions up to 95% when five frames were acquired.

For completeness, image SNR, CNR and Sharpness measures are summarized in Table 2. Compared to the first frame, there was a mild trend towards decline in both SNR and CNR of the later frames (p<0.05). That decline was not statistically significant until the fourth and fifth frames (p<0.05). Edge sharpness loss was not statistically significant in any frames compared to the first frame.

TABLE 2

SNR, CNR, and edge sharpness (mean ± SD) of coronary vessel wall at different time-frames.

| Frame No. | SNR | CNR | Edge Sharpness |
| --- | --- | --- | --- |
| 1 | 21.4 ± 13.4 | 7.2 ± 5.4 | 13.6 ± 6.7 |
| 2 | 18.6 ± 9.0 | 5.9 ± 3.6 | 13.7 ± 6.4 |
| 3 | 18.2 ± 9.2 | 6.2 ± 4.1 | 14.2 ± 7.8 |
| 4 | 16.6 ± 7.9* | 5.0 ± 3.6* | 12.2 ± 6.3 |
| 5 | 16.5 ± 8.5* | 4.6 ± 3.6* | 11.6 ± 7.3 |

*p value < .05, compared to the measurements from the first frame.

Quantitative and Statistical Assessment

The acquisition of multiple images not only improved the success rate of coronary vessel wall imaging but also allowed a choice of the frame with the thinnest wall thickness as the frame with the best view of the coronary for wall thickness measurement. As shown in FIG. 9, the first three frames contributed the most to the thinnest wall measurement with 21%, 26%, and 29% of the cases, respectively. The fourth and fifth frames contributed by a smaller yet considerable share (16% and 8%, respectively).

FIG. 10a displays the effect of using the TRAPD multi-frame thinnest wall thickness rather than the single-frame wall thickness to determine any difference between normal and diseased states. Using the PS-DIR measurements from only the first frame successfully demonstrated a large difference between normal and patient images (p<0.001). However, utilizing consecutive TRAPD frames for quantitative analysis and reporting the minimum mean wall thickness additionally achieved three important results: (1) thinner reported wall measurements in both healthy subjects and patients as indicated by the trend analysis (decline trend, p<0.0001), (2) more separation between the normal and patient wall thickness values, and (3) more precision demonstrated by a narrower standard deviation.

Mann-Whitney tests show statistically significant differences between normals and patients (p<0.001) with a smaller p-value associated with utilization of more time-frames. The repeated-measures ANOVA results demonstrate that, in normals and in patients, separately, vessel wall thickness measurement continues to decline with statistically significant difference (P<0.05) when two or three images were used in calculations in comparison to single frame measurements. The decline in wall thickness measurement does not continue by additionally using the fourth and fifth frames (p=NS). These results agree with the observation from FIG. 10 of the decline in wall thickness measurement if two or three frames were utilized followed later by a horizontal plateau.

In sum, these analyses show, in addition to improved success rate, a more distinct separation between normal and patient minimum wall thickness for three frames or greater analysis (1.07 mm for healthy subjects vs. 1.48 mm for subjects with one or more Framingham risk factors, resulting in a 36% inter-group difference) versus a single frame analysis (1.24 mm for healthy subjects vs. 1.55 mm for subjects with one or more Framingham risk factors, resulting in only a 25% inter-group difference). This can also be analytically appreciated in FIG. 10 where there is less overlap of measurement error bars for three frames or greater versus one frame thickness measurements in normal and at-risk subjects. These analyses also show that greater wall thickness precision was demonstrated by narrower standard deviations when using five frames (0.16 mm for healthy subjects vs. 0.22 mm for subjects with one or more Framingham risk factors) compared to using a single frame (0.20 mm for healthy subjects vs. 0.26 mm for subjects with one or more Framingham risk factors).

Reproducibility

The repeated wall thickness measurements by the first observer showed no statistically significant difference when compared to the reference standard (1.30±0.26 mm vs. 1.29±0.25 mm, p=0.89). Measurements obtained from the first and second scans performed by the first observer were similar as well (1.36±0.28 mm vs. 1.35±0.26 mm, p=0.98). Measurements performed by the second observer showed no statistical significance (1.32±0.27 mm vs. 1.29±0.25 mm, p=0.09).

Figure 11:
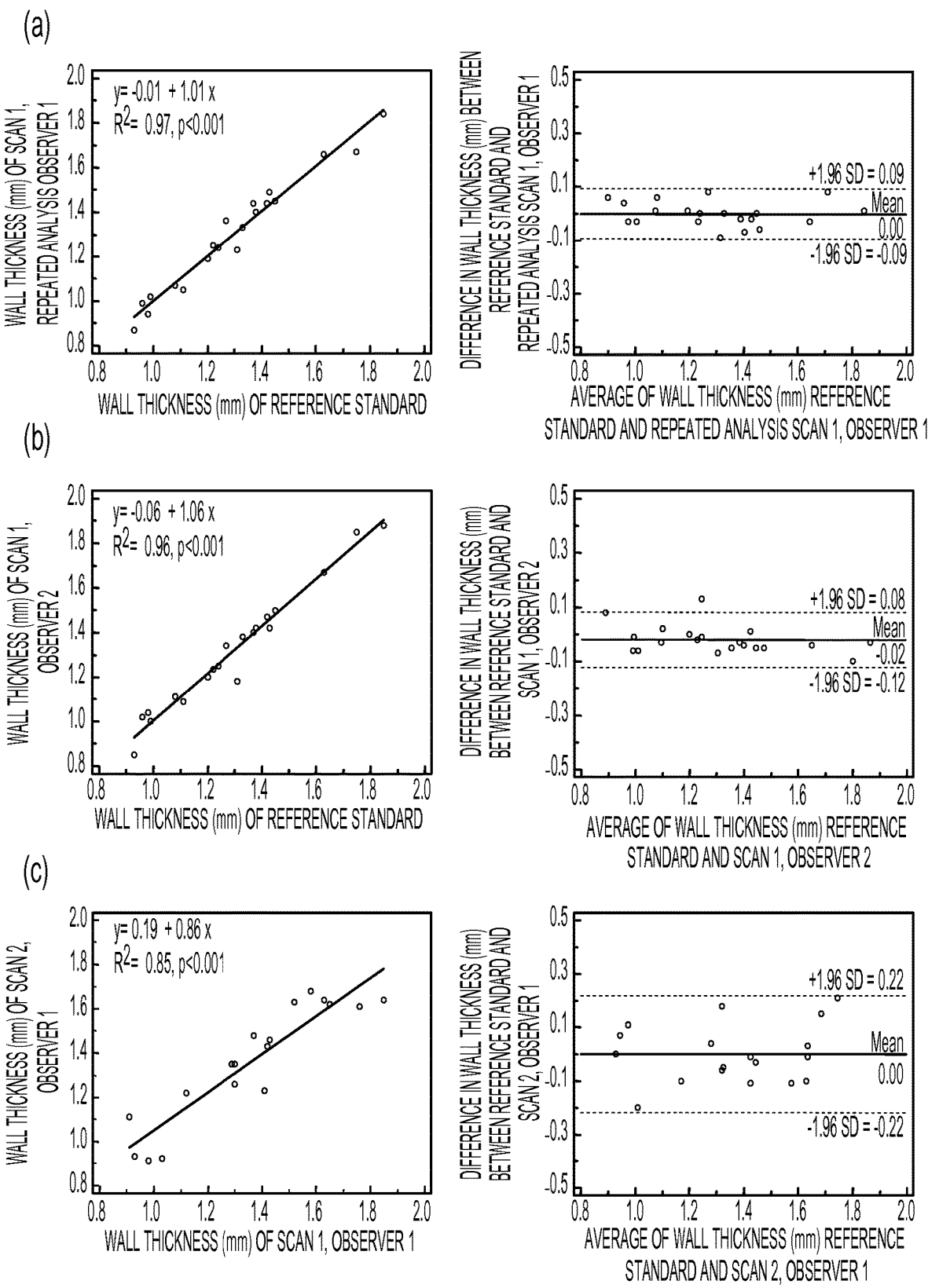
FIG. 11 provides scatter diagrams (left) and Bland-Altman plots (right) of the wall thickness measurements performed by observer 1 using data from scan 1 (reference standard) compared with (a) repeated measurements by same observer 1 and scan 1, (b) measurements performed by observer 2 using data of scan 1, and (c) measurements performed by observer 1 using data of scan 2.

The scatter diagrams and Bland-Altman plots are shown in FIG. 11. The highest correlations were associated with the repeated measurements of the same data by the same observer 1 ($R^2$=0.97, p<0.001) and by different observers ($R^2$=0.96, p<0.001). Interscan measurement correlation was less (R2=0.85, p<0.001). The ICC for wall thickness measurement intraobserver, interobserver, and interscan agreement was 0.98, 0.97, and 0.92, respectively. The CoV was 2.53% for the intraobserver analysis, 2.96% for interobserver analysis, and 5.62% for interscan analysis. The concordance correlation coefficient was 0.98 for the intraobserver analysis, 0.97 for interobserver analysis, and 0.92 for interscan analysis.

Discussion

This study demonstrates that the acquisition of multiple consecutive coronary vessel wall images is feasible with TRAPD imaging and reconstruction. In an earlier study (26), wall thickness measurements from single-frame PS-DIR images with TI as early as 150 ms were shown to correlate well with conventional DIR images at TI=TI*. Phase-sensitive reconstruction alleviated the need to acquire data only during the patient-specific nulling time TI*. Here, the relaxation of that constraint was a key factor in successful coronary wall time-resolved imaging. Indeed, all data in this study were acquired using an invariant TI. Ideally when all images are acquired during complete cardiac rest, cine images will display a still view of the coronary artery wall with time-changing blood signal intensity as in case 1 depicted in FIG. 8. That was also shown in the phantom studies in FIG. 6, which mimicked the steady coronary flow within the time acquisition window at cardiac rest during diastole. However with motion or short diastole, the time-point at which the vessel and slice are optimally aligned varies and is not predicable. In addition, with the complex cardiac-coronary blood flow path and the mixing of inverted and re-inverted blood signal, even DIR at TI=TI* cannot achieve the optimal nulling of blood signal. Thus with time-resolved imaging throughout diastole, only a smaller subset of the images can be of adequate quality (FIG. 8). This subset is more likely to be captured using TRAPD imaging than in conventional single-phase DIR imaging. The first image had adequate quality in only 76% of the cases, which is comparable to conventional single-image DIR techniques (4, 7, 14). With five frames, the percentage of cases with adequate quality scans rose to 95% (FIG. 9), thereby, successfully compensating for slice mispositioning due to residual cardiac motion, aperiodic cardiac and/or unpredicted cardiac and chest wall motions.

Existing solutions including vessel tracking (17-21) and adaptive acquisition (22-25) can add substantial complexity to already challenging coronary artery MRI. Time-resolved PS-DIR provides a relatively simple and robust alternative. In particularly challenging cases, time-resolved PS-DIR can also be utilized in conjunction with those approaches.

Figure 10:
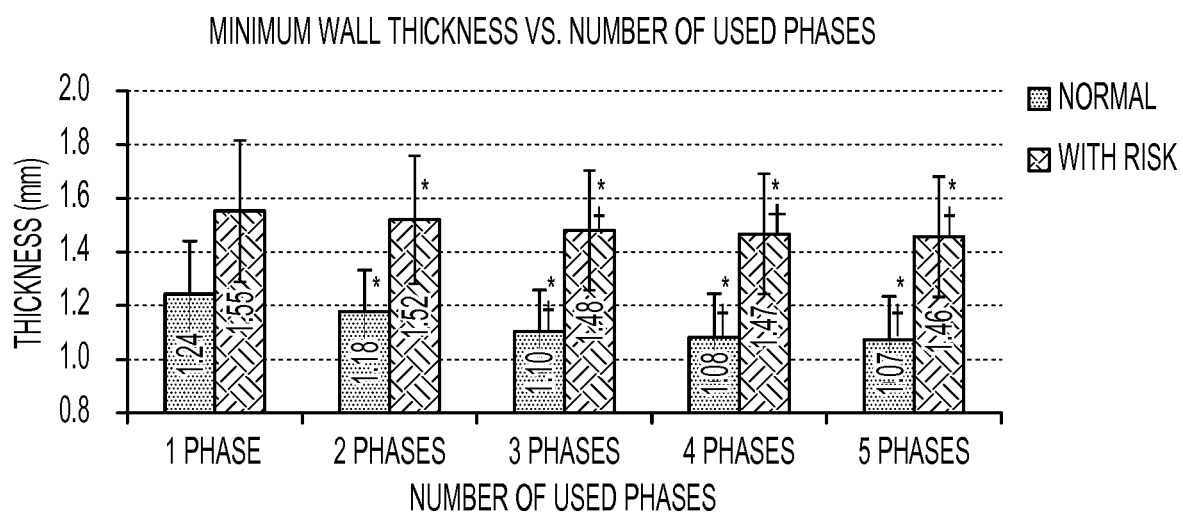
FIG. 10 provides bar graphs showing examples of mean and standard deviation of the minimum wall thickness versus the number of frames used in calculations in normals and subjects with risk factors. An asterisk (*) denotes a p-value<0.05 in comparison to the measurements done using the first frame only. A dagger (†) denotes a p-value<0.05 in comparison to the measurements done using the first two frames only.

With multiple views of the vessel wall in one embodiment of the present subject matter, TRAPD allows one to determine the subject-dependent frame with the minimum perceived wall thickness as an improved method of approximating the actual thickness. During diastole, the variation in apparent wall thickness can be due to several reasons including slow-moving blood or angulated artery relative to the imaged slice (11, 13). With appropriate slice and TD planning, the optimal coronary orientation is most frequently achieved in the early frames. As shown in FIGS. 9 and 10, little improvement is expected in this example by acquiring additional frames beyond the number in this study as those would mostly suffer from excessive motion artifacts and loss of SNR due to the successive fixed flip-angle excitation. In another embodiment of the present subject matter, instead of repeating the acquisition sequence block [535] with each excitation-pulse [536] unaltered, altering the excitation RF pulse constant flip angle in each repetition and using variable ramp flip angle excitation schemes can be employed to improve SNR in some examples.

2D wall imaging in this example provides data only from a single slice per acquisition. However, total acquisition time is considerably shorter than typical 3D coronary wall imaging. This advantage permits TRAPD data to be acquired at multiple sites within a reasonable time duration in this example. In addition to long acquisition time, 3D imaging methods can be challenged in some examples by geometry-sensitive planning and potentially inconsistent suppression of blood signal. Unlike 2D imaging in which the data can be acquired separately at multiple sites, failure of a 3D imaging acquisition in some embodiments can render acquired data unusable and inconvenient to repeat within the commonly-allotted examination time.

In other embodiments, a large slice thickness might lead to volume averaging artifacts. In one embodiment, a slice thickness of 8 mm was the minimum thickness possible when using spectral spatial water-selective excitation. This fat-suppression method was preferred in this example study in order to obtain homogenous fat suppression at all frames, preserve short temporal resolution by avoiding prepulses, and maintain adequate blood-tissue CNR. Although, it is possible to use other pre-imaging fat suppression pulses and hence thinner slices as shown by other studies, this comes at the expense of a reduced SNR.

The results of this example show excellent intraobserver and interobserver agreement demonstrated by the correlation measures of ICC above 0.95, and CoC, with a CoV less than 3% and the statistically insignificant differences in the t-test comparisons. Furthermore, repeated acquisitions in some embodiments demonstrated good reproducibility with a CoV less than 6% and slightly reduced ICC, CoC, and CoV. This reduction can be attributed to the fact that the original and the repeated acquisitions were acquired of the same coronary segment but not precisely at identical locations for this example.

In addition to improving the success rate of coronary vessel wall imaging, TRAPD demonstrated a statistically significant improvement in determining the difference between the wall thickness of healthy and subjects with risk factors for CAD in this example (FIG. 10). Obtaining measurements from the best image of all the time-resolved frames rather than the first single frame resulted in a wider gap between normal and patient mean wall thicknesses (1.07 mm and 1.46 mm vs. 1.24 mm and 1.55 mm) and a narrower spread of measurements represented in the narrower standard deviation (0.16 mm and 0.22 mm vs. 0.20 mm and 0.26 mm) These results imply that TRAPD offers more robust measures of coronary wall thickness and an improved approach for identifying abnormal thickness attributable to various CAD risk factors.

CONCLUSION

Embodiments of the present subject matter implemented fast time-resolved PS-DIR (TRAPD) imaging to improve coronary arterial wall imaging by increasing the success rate of obtaining good to excellent quality images and imaging slice-vessel orthogonality (i.e., slices orthogonal to longitudinal axis of the vessel). This has also resulted in vessel wall thickness measurements that show a more distinct difference between healthy subjects and patient populations.

Biomedical embodiments of the present subject matter have a number of applications. Non-limiting examples include: (1) early detection of vascular disease, (2) research in the field of vascular disease, (3) assessment of the efficacy of medication and/or lifestyle changes in a particular subject, and (4) assessment of the efficacy of new medications or new uses of existing medications to treat vascular disease.

Non-Medical Applications

The subject matter described herein can be applied to problems beyond the medical field. Indeed, the subject matter can be applied to improve imaging in any environment that is subject to periodic movement. Examples of such environments include downhole imaging in well-drilling (wherein drilling fluid is subject to regular pulses caused, for example, by pumps) and imaging in robotic applications, where the motions of a robotic arm can be cyclic.

Implementation in Hardware and/or Software

The methods described herein can be implemented on general-purpose or specially-programmed hardware or software. For example, the methods can be implemented by a computer-readable medium. The computer-readable medium can be non-transitory and/or tangible. For example, the computer readable medium can be volatile memory (e.g., random access memory and the like) or non-volatile memory (e.g., read-only memory, hard disks, floppy discs, magnetic tape, optical discs, paper table, punch cards, and the like).

INCORPORATION BY REFERENCE

All patents, published patent applications, and other references disclosed herein are hereby expressly incorporated by reference in their entireties by reference.

EQUIVALENTS

While the present subject matter has been described with reference to the above embodiments, it will be understood by those skilled in the art that various changes can be made and equivalents can be substituted for elements thereof without departing from the scope of the subject matter. In addition, many modifications can be made to adapt a particular situation or material to the teachings of the subject matter without departing from the essential scope thereof. Therefore, it is intended that the subject matter not be limited to the particular embodiment disclosed as the best mode contemplated for carrying out this subject matter, but that the subject matter will include all embodiments falling within the scope of the appended claims.

The functions of several elements may, in alternative embodiments, be carried out by fewer elements, or a single element. Similarly, in some embodiments, any functional element may perform fewer, or different, operations than those described with respect to the illustrated embodiment. Also, functional elements (e.g., modules, databases, computers, clients, servers and the like) shown as distinct for purposes of illustration may be incorporated within other functional elements, separated in different hardware or distributed in a particular implementation.

While certain embodiments according to the present subject matter have been described, the present subject matter is not limited to just the described embodiments. Various changes and/or modifications can be made to any of the described embodiments without departing from the spirit or scope of the present subject matter. Also, various combinations of elements, steps, features, and/or aspects of the described embodiments are possible and contemplated even if such combinations are not expressly identified herein.

REFERENCES

1. Botnar R M, Stuber M, Kissinger K V, Kim W Y, Spuentrup E, Manning W J. Noninvasive coronary vessel wall and plaque imaging with magnetic resonance imaging. Circulation. 2000; 102(21):2582-7.
2. Fayad Z A, Fuster V, Fallon J T, et al. Noninvasive in vivo human coronary artery lumen and wall imaging using black-blood magnetic resonance imaging. Circulation. 2000; 102(5):506-10.
3. Kim W Y, Stuber M, Bornert P, Kissinger K V, Manning W J, Botnar R M. Three-dimensional black-blood cardiac magnetic resonance coronary vessel wall imaging detects positive arterial remodeling in patients with nonsignificant coronary artery disease. Circulation. 2002; 106(3): 296-9.
4. Miao C, Chen S, Macedo R, et al. Positive remodeling of the coronary arteries detected by magnetic resonance imaging in an asymptomatic population: MESA (Multi-Ethnic Study of Atherosclerosis). J Am Coll Cardiol. 2009; 53(18):1708-15.
5. Glagov S, Weisenberg E, Zarins C K, Stankunavicius R, Kolettis G J. Compensatory enlargement of human atherosclerotic coronary arteries. N Engl J Med. 1987; 316 (22):1371-5.
6. Kim W Y, Astrup A S, Stuber M, et al. Subclinical coronary and aortic atherosclerosis detected by magnetic resonance imaging in type 1 diabetes with and without diabetic nephropathy. Circulation. 2007; 115(2):228-35.
7. Terashima M, Nguyen P K, Rubin G D, et al. Right coronary wall CMR in the older asymptomatic advance cohort: positive remodeling and associations with type 2 diabetes and coronary calcium. J Cardiovasc Magn Reson. 2010; 12:75.
8. Tangcharoen T, Jahnke C, Koehler U, et al. Impact of heart rate variability in patients with normal sinus rhythm on image quality in coronary magnetic angiography. Journal of magnetic resonance imaging: JMRI. 2008; 28:74-9.
9. Jahnke C, Nehrke K, Paetsch I, et al. Improved bulk myocardial motion suppression for navigator-gated coronary magnetic resonance imaging. Journal of magnetic resonance imaging: JMRI. 2007; 26:780-6.
10. Horiguchi J, Fukuda H, Yamamoto H, et al. The impact of motion artifacts on the reproducibility of repeated coronary artery calcium measurements. European radiology. 2007; 17:81-6.
11. Schar M, Kim W Y, Stuber M, Boesiger P, Manning W J, Botnar R M. The impact of spatial resolution and respiratory motion on M R imaging of atherosclerotic plaque. Journal of magnetic resonance imaging: JMRI. 2003; 17:538-44.
12. Kim W Y, Stuber M, Kissinger K V, Andersen N T, Manning W J, Botnar R M. Impact of bulk cardiac motion on right coronary M R angiography and vessel wall imaging. Journal of magnetic resonance imaging: JMRI. 2001; 14:383-90.
13. Antiga L, Wasserman B A, Steinman D A. On the overestimation of early wall thickening at the carotid bulb by black blood MRI, with implications for coronary and vulnerable plaque imaging. Magn Reson Med. 2008; 60(5):1020-8.
14. Kim W Y, Stuber M, Kissinger K V, Andersen N T, Manning W J, Botnar R M. Impact of bulk cardiac motion on right coronary M R angiography and vessel wall imaging. J Magn Reson Imaging. 2001; 14(4):383-90.
15. Scott A D, Keegan J, Firmin D N. Motion in cardiovascular M R imaging. Radiology. 2009; 250(2):331-51.
16. Macedo R, Chen S, Lai S, et al. MRI detects increased coronary wall thickness in asymptomatic individuals: the multi-ethnic study of atherosclerosis (MESA). J Magn Reson Imaging. 2008; 28(5):1108-15.
17. Foo T K, Ho V B, Hood M N. Vessel tracking: prospective adjustment of section-selective M R angiographic locations for improved coronary artery visualization over the cardiac cycle. Radiology. 2000; 214(1):283-9.
18. Gatehouse P D, Keegan J, Yang G Z, Mohiaddin R H, Firmin D N. Tracking local volume 3D-echo-planar coronary artery imaging. Magn Reson Med. 2001; 46(5):1031-6.

19. Saranathan M, Ho V B, Hood M N, Foo T K, Hardy C J. Adaptive vessel tracking: automated computation of vessel trajectories for improved efficiency in 2D coronary M R angiography. J Magn Reson Imaging. 2001; 14(4):368-73.
20. Dewan M, Hager G D, Lorenz C H. Image-based coronary tracking and beat-to-beat motion compensation: feasibility for improving coronary M R angiography. Magn Reson Med. 2008; 60(3):604-15.
21. Scott A D, Keegan J, Firmin D N. High-resolution 3D coronary vessel wall imaging with near 100% respiratory efficiency using epicardial fat tracking: reproducibility and comparison with standard methods. J Magn Reson Imaging. 2011; 33(1):77-86.
22. Plein S, Jones T R, Ridgway J P, Sivananthan M U. Three-dimensional coronary M R angiography performed with subject-specific cardiac acquisition windows and motion-adapted respiratory gating. AJR Am J Roentgenol. 2003; 180(2):505-12.
23. Hoffmann M H K, Lessick J, Manzke R, et al. Automatic determination of minimal cardiac motion phases for computed tomography imaging: initial experience. European radiology. 2006; 16:365-73.
24. Ustun A, Desai M, Abd-Elmoniem K Z, Schar M, Stuber M. Automated identification of minimal myocardial motion for improved image quality on M R angiography at 3 T. AJR American journal of roentgenology. 2007; 188:W283-90.
25. Roes S D, Korosoglou G, Schar M, et al. Correction for heart rate variability during 3D whole heart M R coronary angiography. Journal of magnetic resonance imaging: JMRI. 2008; 27:1046-53.
26. Abd-Elmoniem K Z, Weiss R G, Stuber M. Phase-sensitive black-blood coronary vessel wall imaging. Magn Reson Med. 2010; 63(4):1021-30.
27. Fleckenstein J L, Archer B T, Barker B A, Vaughan J T, Parkey R W, Peshock R M. Fast short-tau inversion-recovery M R imaging. Radiology. 1991; 179(2):499-504.
28. Xie J, Bi X, Fan Z, et al. 3D flow-independent peripheral vessel wall imaging using T(2)-prepared phase-sensitive inversion-recovery steady-state free precession. J Magn Reson Imaging. 2010; 32(2):399-408.
29. Spuentrup E, Stuber M, Botnar R M, Manning W J. The impact of navigator timing parameters and navigator spatial resolution on 3D coronary magnetic resonance angiography. Journal of magnetic resonance imaging: JMRI. 2001; 14:311-8.
30. Sakuma H, Ichikawa Y, Chino S, Hirano T, Makino K, Takeda K. Detection of coronary artery stenosis with whole-heart coronary magnetic resonance angiography. J Am Coll Cardiol. 2006; 48(10):1946-50.
31. Stuber M, Weiss R G. Coronary magnetic resonance angiography. J Magn Reson Imaging. 2007; 26(2):219-34.
32. Johnson K R, Patel S J, Whigham A, Hakim A, Pettigrew R I, Oshinski J N. Three-dimensional, time-resolved motion of the coronary arteries. J Cardiovasc Magn Reson. 2004; 6(3):663-73.
33. Husmann L, Leschka S, Desbiolles L, et al. Coronary artery motion and cardiac phases: dependency on heart rate—implications for C T image reconstruction. Radiology. 2007; 245(2):567-76.
34. Meyer C H, Pauly J M, Macovski A, Nishimura D G. Simultaneous spatial and spectral selective excitation. Magn Reson Med. 1990; 15(2):287-304.
35. Fischer S E, Wickline S A, Lorenz C H. Novel real-time R-wave detection algorithm based on the vectorcardiogram for accurate gated magnetic resonance acquisitions. Magn Reson Med. 1999; 42(2):361-70.
36. Etienne A, Botnar R M, Van Muiswinkel A M, Boesiger P, Manning W J, Stuber M. "Soap-Bubble" visualization and quantitative analysis of 3D coronary magnetic resonance angiograms. Magn Reson Med. 2002; 48(4):658-66.
37. Gharib A M, Ho V B, Rosing D R, et al. Coronary artery anomalies and variants: technical feasibility of assessment with coronary M R angiography at 3 T. Radiology. 2008; 247(1):220-7.
38. Stuber M, Botnar R M, Danias P G, Kissinger K V, Manning W J. Submillimeter three-dimensional coronary M R angiography with real-time navigator correction: comparison of navigator locations. Radiology. 1999; 212(2):579-87.
39. Danias P G, McConnell M V, Khasgiwala V C, Chuang M L, Edelman R R, Manning W J. Prospective navigator correction of image position for coronary M R angiography. Radiology. 1997; 203(3):733-6.
40. Wang Y, Ehman R L. Retrospective adaptive motion correction for navigator-gated 3D coronary M R angiography. J Magn Reson Imaging. 2000; 11(2):208-14.
41. Stuber M, Botnar R M, Spuentrup E, Kissinger K V, Manning W J. Three-dimensional high-resolution fast spin-echo coronary magnetic resonance angiography. Magn Reson Med. 2001; 45(2):206-11.
42. Malayeri A A, Macedo R, Li D, et al. Coronary vessel wall evaluation by magnetic resonance imaging in the multi-ethnic study of atherosclerosis: determinants of image quality. J Comput Assist Tomogr. 2009; 33(1):1-7.
43. Botnar R M, Stuber M, Danias P G, Kissinger K V, Manning W J. Improved coronary artery definition with T2-weighted, free-breathing, three-dimensional coronary MRA. Circulation. 1999; 99(24):3139-48.
44. Bland J M, Altman D G. Statistical methods for assessing agreement between two methods of clinical measurement. Lancet. 1986; 1(8476):307-10.
45. Lin L I. A concordance correlation coefficient to evaluate reproducibility. Biometrics. 1989; 45(1):255-68.

What is claimed is:
1. An imaging method comprising:
receiving a trigger signal;
after a period equal to a trigger delay minus an inversion delay, applying a single non-selective inversion radiofrequency pulse to a region of interest followed by a single slice-selective reinversion radiofrequency pulse to a slice of the region of interest of a subject;
after lapse of the trigger delay commenced at the trigger signal, acquiring a plurality of time-resolved cine images using an acquired k-space for each individual image using both phase and magnitude components of the k-space of the slice of the region of interest of the subject to obtain a plurality of time-resolved cine image frames of a vessel wall with an acquisition window of as short as 20 ms or less for each time-resolved cine image frame of the plurality of time-resolved cine image frames, wherein the plurality of time-resolved cine image frames are each a phase-sensitive, signed-magnitude, time-resolved image obtained using the entire acquired k-space;
applying a navigator pulse directly before acquiring the plurality of time-resolved cine images; and
tracking lung motion in order to compensate for lung-motion-induced changes in an anatomical location of the region of interest of the subject.

2. The method of claim 1, wherein the trigger signal is a cardiac cycle signal.

3. The method of claim 2, wherein the cardiac cycle signal is an R-wave.

4. The method of claim 2, wherein the trigger delay corresponds to the time period between the cardiac cycle signal and a period of minimal myocardial motion.

5. The method of claim 1, wherein the region of interest is a blood vessel.

6. The method of claim 5, wherein the blood vessel is a coronary artery.

7. The method of claim 5, wherein the blood vessel is a peripheral vessel.

8. The method of claim 7, wherein the peripheral vessel is selected to include at least one of:
a carotid artery, a femoral artery, a pulmonary artery, a gastrointestinal vessel, and a renal artery.

9. The method of claim 1, wherein the plurality of time-resolved cine image frames are consecutive.

10. The method of claim 9, wherein a temporal offset between the plurality of time-resolved cine image frames is substantially uniform.

11. The method of claim 10, wherein the temporal offset is between about 5 ms and about 50 ms.

12. The method of claim 1, wherein the plurality of time-resolved cine image frames are captured between 150 ms and about 225 ms after application of the non-selective inversion radiofrequency pulse.

13. The method of claim 1, further comprising:
storing the plurality of time-resolved cine image frames in a non-transitory computer-readable medium.

14. The method of claim 1, further comprising:
presenting the plurality of time-resolved cine image frames to a user;
receiving a selection of one or more images from the plurality of time-resolved cine image frames; and
calculating vessel thickness based on the one or more images.

15. The method of claim 14, wherein at least 75% of a vessel of interest is visible in the one or more images.

16. The method of claim 1, wherein the trigger signal is based on a cardiac cycle; and
wherein the method is repeated: every cardiac cycle, every other cardiac cycle, or every nth cardiac cycle, wherein n is a positive integer.

17. The method of claim 1, wherein at least 75% of a vessel of interest is visible in at least one of the plurality of time-resolved cine image frames.

18. The method of claim 1, wherein the slice of the region of interest contains a cross-section of a vessel and wherein the method further comprises:
calculating a thickness of the vessel.

19. The method of claim 1, wherein the slice is a two-dimensional slice.

20. The method of claim 1, wherein the slice is a three-dimensional slice.

21. The imaging method of claim 1, further comprising:
determining a magnetic field phase of a vessel lumen image region, the vessel image lumen region comprising blood lumen, the vessel wall, and surrounding tissue zones;
utilizing discrepancies and polarity variations of the magnetic field phase of the vessel lumen image region of each of the plurality of time-resolved cine image frames to obtain a polarity image of the vessel wall and lumen; and
utilizing the polarity image of the vessel wall and lumen with a magnitude image of the plurality of time-resolved cine image frames to obtain multiple signed-magnitude images of the vessel wall at different time points.

22. A non-transitory computer readable medium containing program instructions that, when executed by a computer, configure the computer to:
receive a trigger signal;
after a period equal to a trigger delay minus an inversion delay, apply a single non-selective inversion radiofrequency pulse to a region of interest followed by a single slice-selective reinversion radiofrequency pulse to a slice of the region of interest of a subject;
after lapse of the trigger delay commenced at the trigger signal, acquire a plurality of time-resolved cine images of the slice of the region of interest of the subject from an imaging device using an acquired k-space for each individual image using both the phase and magnitude components of the k-space to obtain a plurality of time-resolved cine image frames with an acquisition window of as short as 20 ms or less for each time-resolved cine image frame of the plurality of time-resolved cine image frames, wherein the plurality of time-resolved cine image frames are each a phase-sensitive, signed-magnitude, time-resolved image obtained using the entire acquired k-space;
applying a navigator pulse directly before acquiring the plurality of time-resolved cine images; and
tracking lung motion in order to compensate for lung-motion-induced changes in an anatomical location of the region of interest of the subject.

23. A magnetic resonance imaging device comprising:
a magnetic field gradient controller programmed to control operation of a magnetic field gradient amplifier to alter a spinning frequency of atomic nuclei within a subject;
a radio frequency pulse controller programmed to control operation of a radiofrequency transmitter to apply radiofrequency pulses to a region of interest within the subject;
an analog/digital signal converter programmed to convert analog signals received by a radiofrequency receiver coil; and
an imaging sequence controller programmed to:
receive a trigger signal;
instruct the radiofrequency pulse controller to, after a period equal to a trigger delay minus an inversion delay, apply a single non-selective inversion radiofrequency pulse to the region of interest followed by a single slice-selective reinversion radiofrequency pulse to a slice of the region of interest;
instruct the analog/digital signal converter to, after lapse of the trigger delay commenced at the trigger signal, acquire a plurality of time-resolved cine images of the slice of the region of interest from an imaging device using an acquired k-space for each individual image using both phase and magnitude components of the k-space to obtain a plurality of time-resolved cine image frames with an acquisition window of as short as 20 ms or less for each time-resolved cine image frame of the plurality of time-resolved cine image frames, wherein the plurality of time-resolved cine image frames are each a phase-sensitive, signed-magnitude, time-resolved image obtained using the entire acquired k-space;

instruct application of a navigator pulse directly before acquiring the plurality of cine image frames; and
instruct tracking lung motion to compensate for lung-motion-induced changes in an anatomical location of the region of interest.

24. The magnetic resonance imaging device of claim 23, wherein at least 75% of a vessel of interest is visible in at least one of the plurality of cine image frames.

* * * * *